(12) United States Patent
Short et al.

(10) Patent No.: US 12,144,377 B2
(45) Date of Patent: Nov. 19, 2024

(54) ABSORBENT CONTAINING MOUTHPIECE FOR AEROSOL DELIVERY DEVICE

(71) Applicant: RAI Strategic Holdings, Inc., Winston-Salem, NC (US)

(72) Inventors: Jason M. Short, Winston-Salem, NC (US); Sawyer A. Hubbard, Winston-Salem, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 484 days.

(21) Appl. No.: 17/449,690

(22) Filed: Oct. 1, 2021

(65) Prior Publication Data

US 2023/0105080 A1 Apr. 6, 2023

(51) Int. Cl.
*A24F 40/485* (2020.01)
*A24F 7/00* (2006.01)
*A24F 40/10* (2020.01)
*A61M 15/06* (2006.01)

(52) U.S. Cl.
CPC .............. *A24F 40/485* (2020.01); *A24F 7/00* (2013.01); *A24F 40/10* (2020.01); *A61M 15/06* (2013.01)

(58) Field of Classification Search
CPC ........... A24F 40/10; A24F 40/42; A24F 40/50
See application file for complete search history.

(56) References Cited

U.S. PATENT DOCUMENTS 2,057,353 A 10/1936 Whittemore, Jr.
2,104,266 A 1/1938 McCormick
3,200,819 A 8/1965 Gilbert
4,922,901 A 5/1990 Brooks et al.
(Continued)

FOREIGN PATENT DOCUMENTS

CN 1541577 11/2004
CN 2719043 8/2005
(Continued)

OTHER PUBLICATIONS

International Search Report mailed Dec. 23, 2022 in the corresponding International Patent Application No. PCT/IB2022/059319. 4 pages.

*Primary Examiner* — Truc T Nguyen
(74) *Attorney, Agent, or Firm* — Womble Bond Dickinson (US) LLP

(57) ABSTRACT

The present disclosure provides an aerosol consumable device. In some cases, the aerosol consumable device includes at a first end, a mouthpiece portion having a top surface comprising two or more crescent-shaped openings arranged on opposite sides of an aerosol cap having a closed end. The aerosol consumable device further comprises a liquid absorbing insert positioned within the mouthpiece portion between the first end and a second end opposite the first end, and an aerosol tube positioned between the liquid absorbing insert and the second end. The liquid absorbing insert defines an internal aerosol channel. Upon a draw on the mouthpiece portion by a user, a first portion of aerosol generated by the aerosol consumable device travels through the internal aerosol channel and through the crescent-shaped openings and the aerosol tube is configured to direct accumulated droplets on an inner surface of the aerosol tube into the liquid absorbing insert.

21 Claims, 11 Drawing Sheets

(56) References Cited

U.S. PATENT DOCUMENTS

| | | |
|---|---|---|
| 5,060,671 A | 10/1991 | Counts et al. |
| 5,093,894 A | 3/1992 | Deevi et al. |
| 5,894,841 A | 4/1999 | Voges |
| 6,125,853 A | 10/2000 | Susa et al. |
| 6,155,268 A | 12/2000 | Takeuchi |
| 7,117,867 B2 | 10/2006 | Cox et al. |
| 7,832,410 B2 | 11/2010 | Hon |
| 8,314,591 B2 | 11/2012 | Terry et al. |
| 8,365,742 B2 | 2/2013 | Hon |
| 8,499,766 B1 | 8/2013 | Newton |
| 8,528,569 B1 | 9/2013 | Newton |
| 8,833,364 B2 | 9/2014 | Buchberger |
| 9,220,304 B2 | 12/2015 | Greim |
| 9,462,831 B2 | 10/2016 | Liu |
| 9,877,508 B2 | 1/2018 | Kane |
| 10,015,990 B2 | 7/2018 | Mironov |
| 10,028,537 B1 | 7/2018 | Hawes et al. |
| 10,058,125 B2 | 8/2018 | Worm et al. |
| 10,080,851 B2 | 9/2018 | Davidson et al. |
| 10,085,481 B2 | 10/2018 | Verleur et al. |
| 10,092,037 B2 | 10/2018 | Tucker et al. |
| 10,104,911 B2 | 10/2018 | Thorens et al. |
| 10,104,913 B2 | 10/2018 | Lau et al. |
| 10,117,463 B2 | 11/2018 | Thomas |
| 10,117,467 B2 | 11/2018 | Hawes et al. |
| 2005/0016550 A1 | 1/2005 | Katase |
| 2006/0196518 A1 | 9/2006 | Hon |
| 2008/0092912 A1 | 4/2008 | Robinson et al. |
| 2009/0095311 A1 | 4/2009 | Hon |
| 2009/0126745 A1 | 5/2009 | Hon |
| 2009/0151717 A1 | 6/2009 | Bowen et al. |
| 2009/0188490 A1 | 7/2009 | Hon |
| 2009/0272379 A1 | 11/2009 | Thorens et al. |
| 2009/0320863 A1 | 12/2009 | Fernando et al. |
| 2011/0094523 A1 | 4/2011 | Thorens et al. |
| 2011/0126848 A1 | 6/2011 | Zuber et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2013/0037041 A1 | 2/2013 | Worm et al. |
| 2013/0042865 A1 | 2/2013 | Monsees et al. |
| 2013/0306084 A1 | 11/2013 | Flick |
| 2013/0319435 A1 | 12/2013 | Flick |
| 2014/0000638 A1 | 1/2014 | Sebastian et al. |
| 2014/0096781 A1 | 4/2014 | Sears et al. |
| 2014/0096782 A1 | 4/2014 | Ampolini et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0366898 A1 | 12/2014 | Monsees et al. |
| 2015/0020832 A1 | 1/2015 | Greim et al. |
| 2015/0150308 A1 | 6/2015 | Monsees et al. |
| 2015/0164142 A1 | 6/2015 | Li et al. |
| 2015/0208729 A1 | 7/2015 | Monsees et al. |
| 2015/0313287 A1 | 11/2015 | Verleur et al. |
| 2017/0027226 A1 | 2/2017 | Mironov et al. |
| 2017/0071256 A1 | 3/2017 | Verleur et al. |
| 2017/0095005 A1 | 4/2017 | Monsees et al. |
| 2017/0135404 A1 | 5/2017 | Reevell |
| 2017/0135405 A1 | 5/2017 | Reevell |
| 2017/0143042 A1 | 5/2017 | Batista et al. |
| 2017/0215485 A1 | 8/2017 | Zitzke |
| 2017/0231281 A1 | 8/2017 | Hatton et al. |
| 2017/0231282 A1 | 8/2017 | Hatton et al. |
| 2017/0281883 A1 | 10/2017 | Li et al. |
| 2017/0325289 A1 | 11/2017 | Liu |
| 2017/0340011 A1 | 11/2017 | Batista |
| 2017/0340012 A1 | 11/2017 | Mironov et al. |
| 2017/0347711 A1 | 12/2017 | Litten et al. |
| 2017/0347712 A1 | 12/2017 | Singh |
| 2018/0000157 A1 | 1/2018 | Batista et al. |
| 2018/0000160 A1 | 1/2018 | Taschner et al. |
| 2018/0014575 A1 | 1/2018 | Fursa |
| 2018/0020731 A1 | 1/2018 | Rasmussen et al. |
| 2018/0020736 A1 | 1/2018 | Silvestrini |
| 2018/0035717 A1 | 2/2018 | Batista |
| 2018/0042306 A1 | 2/2018 | Atkins et al. |
| 2018/0043114 A1 | 2/2018 | Bowen et al. |
| 2018/0077967 A1 | 3/2018 | Hatton et al. |
| 2018/0084831 A1 | 3/2018 | Mironov |
| 2018/0103685 A1 | 4/2018 | Yener |
| 2018/0132525 A1 | 5/2018 | Patil et al. |
| 2018/0140019 A1 | 5/2018 | Guo et al. |
| 2018/0177230 A1 | 6/2018 | Hawes et al. |
| 2018/0213850 A1 | 8/2018 | Brinkley et al. |
| 2018/0242643 A1 | 8/2018 | Silvestrini et al. |
| 2018/0280637 A1 | 10/2018 | Mayle et al. |
| 2018/0295888 A1 | 10/2018 | Newcomb et al. |
| 2018/0296777 A1 | 10/2018 | Terry et al. |
| 2019/0014826 A1* | 1/2019 | Thorens ............. A61M 16/202 |
| 2019/0364957 A1 | 12/2019 | Fu et al. |
| 2020/0376208 A1* | 12/2020 | Spencer ................. A24F 40/40 |
| 2021/0052095 A1* | 2/2021 | Bisbicis ................ A47G 21/185 |
| 2022/0117299 A1* | 4/2022 | Aller ....................... A24F 40/60 |
| 2022/0312846 A1* | 10/2022 | Jackson ................ H05B 6/065 |
| 2022/0312848 A1* | 10/2022 | Jackson ................ H05B 6/105 |
| 2022/0401661 A1* | 12/2022 | Hunter ............. A61M 15/0085 |
| 2023/0105080 A1* | 4/2023 | Short ..................... A24F 40/10 |
| | | 131/329 |
| 2024/0081400 A1* | 3/2024 | Aller ..................... A24F 40/60 |

FOREIGN PATENT DOCUMENTS

| | | | |
|---|---|---|---|
| CN | 201379072 | 1/2010 | |
| CN | 211510585 U | 9/2020 | |
| CN | 3725170 | * 10/2020 | ............ A24F 40/42 |
| EP | 1 618 803 | 1/2006 | |
| WO | WO 2004/080216 | 9/2004 | |
| WO | WO 2005/099494 | 10/2005 | |
| WO | WO 2007/131449 | 11/2007 | |
| WO | WO 2009135729 | * 11/2009 | .......... A61M 11/002 |
| WO | WO 2016/026811 | 2/2016 | |
| WO | WO 2017/051006 | 9/2016 | |
| WO | WO 2016/207442 | 5/2017 | |
| WO | WO 2018/167166 | 9/2018 | |
| WO | WO 2018/202732 | 11/2018 | |
| WO | 2021/138876 A1 | 7/2021 | |

* cited by examiner

150

152

108

ATOMIZER
106

AEROSOL PRECURSOR
RESERVOIR
104

FIG. 6

ABSORBENT CONTAINING MOUTHPIECE FOR AEROSOL DELIVERY DEVICE

FIELD OF THE DISCLOSURE

The present disclosure relates to aerosol delivery devices such as smoking articles, and more particularly to mouthpieces for aerosol delivery devices such as mouthpieces for smoking articles, electronic cigarettes, and the like.

BACKGROUND

Many smoking articles have been proposed through the years as improvements upon, or alternatives to, smoking products based upon combusting tobacco. Example alternatives have included devices wherein a solid or liquid fuel is combusted to transfer heat to tobacco or wherein a chemical reaction is used to provide such heat source. Examples include the smoking articles described in U.S. Pat. No. 9,078,473 to Worm et al., which is incorporated herein by reference in its entirety.

The point of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., which are incorporated herein by reference. See also, for example, the various types of smoking articles, aerosol delivery devices and electrically powered heat generating sources referenced by brand name and commercial source in U.S. Pat. App. Pub. No. 2015/0220232 to Bless et al., which is incorporated herein by reference. Additional types of smoking articles, aerosol delivery devices and electrically powered heat generating sources referenced by brand name and commercial source are listed in U.S. Pat. App. Pub. No. 2015/0245659 to DePiano et al., which is also incorporated herein by reference in its entirety. Other representative cigarettes or smoking articles that have been described and, in some instances, been made commercially available include those described in U.S. Pat. No. 4,735,217 to Gerth et al.; U.S. Pat. Nos. 4,922,901, 4,947,874, and 4,947,875 to Brooks et al.; U.S. Pat. No. 5,060,671 to Counts et al.; U.S. Pat. No. 5,249,586 to Morgan et al.; U.S. Pat. No. 5,388,594 to Counts et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,726,320 to Robinson et al.; U.S. Pat. No. 7,896,006 to Hamano; U.S. Pat. No. 6,772,756 to Shayan; U.S. Pat. App. Pub. No. 2009/0095311 to Hon; U.S. Pat. App. Pub. Nos. 2006/0196518, 2009/0126745, and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; and WO 2010/091593 to Hon, which are incorporated herein by reference.

Various manners and methods for assembling smoking articles that possess a plurality of sequentially arranged segmented components have been proposed. See, for example, the various types of assembly techniques and methodologies set forth in U.S. Pat. No. 5,469,871 to Barnes et al. and U.S. Pat. No. 7,647,932 to Crooks et al.; and U.S. Pat. App. Pub. Nos. 2010/0186757 to Crooks et al.; 2012/0042885 to Stone et al., and 2012/00673620 to Conner et al.; each of which is incorporated by reference herein in its entirety.

Certain types of cigarettes that employ carbonaceous fuel elements have been commercially marketed under the brand names "Premier," "Eclipse" and "Revo" by R. J. Reynolds Tobacco Company. See, for example, those types of cigarettes described in Chemical and Biological Studies on New Cigarette Prototypes that Heat Instead of Burn Tobacco, R. J. Reynolds Tobacco Company Monograph (1988) and Inhalation Toxicology, 12:5, p. 1-58 (2000). Additionally, a similar type of cigarette has been marketed in Japan by Japan Tobacco Inc. under the brand name "Steam Hot One."

In some instances, some smoking articles, especially those that include a liquid based aerosol precursor, produce accumulated droplets that are unpleasant to smoking article users. Accumulated droplets occur when e-liquid builds up (by various mechanisms) in the flowtube of the smoking article and passes into the consumer or user's mouth as large, conspicuous droplets. The droplets are unwanted and provide an unpleasant experience when using the smoking article for the user.

As such, it would be desirable to provide smoking articles that address one or more of the technical problems sometimes associated with traditional types of smoking articles. In addition, it would be desirable to provide a smoking article that is easy to use and that provides reusable and/or replaceable components.

BRIEF SUMMARY

The present disclosure relates to aerosol delivery devices and mouthpieces for use with aerosol delivery devices. The present disclosure includes, without limitation, the following example implementations:

Example Implementation 1: An aerosol consumable device comprising at a first end, a mouthpiece portion configured for insertion into the mouth of a user for delivery of an aerosol generated by the aerosol consumable device, the mouthpiece portion having a top surface comprising two or more crescent-shaped openings arranged on opposite sides of an aerosol cap having a closed end, at a second end, opposite the first end, a connecting portion configured to be attached to a controller portion of an aerosol delivery device, a liquid absorbing insert positioned within the mouthpiece portion between the first end and the second end, and an aerosol tube positioned between the second end and the liquid absorbing insert, wherein the liquid absorbing insert comprises an absorbent material and defines an internal aerosol channel, and wherein, upon a draw on the mouthpiece portion by the user, a first portion of the aerosol generated by the aerosol consumable device travels through the internal aerosol channel of the liquid absorbing insert and through the two or more crescent-shaped openings, and wherein the aerosol tube is configured to direct accumulated droplets along an inner surface of the aerosol tube into the liquid absorbing insert.

Example Implementation 2: The aerosol consumable device of Example Implementation 1, or any combination of preceding example implementations, wherein when positioned within the mouthpiece portion, the liquid absorbing insert has an oblong tube shape.

Example Implementation 3: The aerosol consumable device of any one of any one of Example Implementations 1-2, or any combination of preceding example implementations, wherein the aerosol tube defines a central axis substantially aligned with a central axis defined by the internal aerosol channel of the liquid absorbing insert.

Example Implementation 4: The aerosol consumable device of any one of Example Implementations 1-3, or any combination of preceding example implementations, wherein the liquid absorbing insert defines a first end and a second end, wherein the aerosol tube defines a first end proximate the second end of the liquid absorbing insert, and wherein the first end of the aerosol tube extends outwardly such that an inner diameter of the first end of the aerosol tube proximate the liquid absorbing insert is greater than a maximum diameter of the internal aerosol channel of the liquid absorbing insert.

Example Implementation 5: The aerosol consumable device of any one of Example Implementations 1-4, or any combination of preceding example implementations, wherein the liquid absorbing insert defines a first end and a second end, wherein the aerosol tube defines a first end proximate the second end of the liquid absorbing insert, and wherein the first end of the aerosol tube extends outwardly such that an inner diameter of the first end of the aerosol tube is substantially the same as a maximum diameter of the internal aerosol channel of the liquid absorbing insert.

Example Implementation 6: The aerosol consumable device of any one of Example Implementations 1-5, or any combination of preceding example implementations, wherein the aerosol cap further defines an open end opposite the closed end thereby creating a cavity in the aerosol cap, and wherein the cavity is configured to trap a second portion of the aerosol generated by the aerosol consumable device.

Example Implementation 7: The aerosol consumable device of any one of Example Implementations 1-6, or any combination of preceding example implementations, wherein the aerosol cap defines a sidewall between the closed end and the open end.

Example Implementation 8: The aerosol consumable device of any one of Example Implementations 1-7, or any combination of preceding example implementations, wherein the liquid absorbing insert defines a first end and a second end, wherein the first end of the liquid absorbing insert is located downstream from the second end of the liquid absorbing insert, and wherein the open end of the aerosol cap is located downstream from the first end of the liquid absorbing insert.

Example Implementation 9: The aerosol consumable device of any one of Example Implementations 1-8, or any combination of preceding example implementations, wherein the liquid absorbing insert defines a first end and a second end, wherein the first end of the liquid absorbing insert is located downstream from the second end of the liquid absorbing insert, and wherein the first end of the liquid absorbing insert is located proximate the open end of the aerosol cap.

Example Implementation 10: The aerosol consumable device of any one of Example Implementations 1-9, or any combination of preceding example implementations, wherein the liquid absorbing insert defines a first end and a second end, wherein the first end of the liquid absorbing insert is located downstream from the second end of the liquid absorbing insert, and wherein the first end of the liquid absorbing insert is located downstream from the open end of the aerosol cap.

Example Implementation 11: The aerosol consumable device of any one of Example Implementations 1-10, or any combination of preceding example implementations, wherein the cavity of the aerosol cap includes a plug configured to absorb the second portion of the aerosol.

Example Implementation 12: The aerosol consumable device of any one of Example Implementations 1-11, or any combination of preceding example implementations, wherein the aerosol cap defines a sidewall between the closed end and the open end, and wherein a portion of an outer surface of the sidewall is chamfered.

Example Implementation 13: The aerosol consumable device of any one of Example Implementations 1-12, or any combination of preceding example implementations, wherein the chamfered portion of the outer surface of the sidewall is located at the open end of the aerosol cap and is configured to direct the first portion of the aerosol through the crescent-shaped openings.

Example Implementation 14: The aerosol consumable device of any one of Example Implementations 1-13, or any combination of preceding example implementations, wherein the chamfered portion of the outer surface of the sidewall is located at the closed end of the aerosol cap and is configured to direct the first portion of the aerosol into the mouth of the user.

Example Implementation 15: The aerosol consumable device of any one of Example Implementations 1-14, or any combination of preceding example implementations, wherein the aerosol cap defines a sidewall between the closed end and the open end, and wherein a portion of an inner surface of the sidewall is chamfered to direct a second portion of the aerosol into the cavity.

Example Implementation 16: The aerosol consumable device of any one of Example Implementations 1-15, or any combination of preceding example implementations, wherein each of the two or more crescent-shaped openings is arranged around a peripheral outer surface of the aerosol cap.

Example Implementation 17: The aerosol consumable device of any one of Example Implementations 1-16, or any combination of preceding example implementations, wherein the closed end of the aerosol cap defines an outer surface, and wherein the outer surface of the closed end of the aerosol cap is raised above at least part of the top surface of the of the first end of the aerosol consumable device.

Example Implementation 18: The aerosol consumable device of any one of Example Implementations 1-17, or any combination of preceding example implementations, wherein the aerosol cap has a substantially cylindrical shape.

Example Implementation 19: The aerosol consumable device of any one of Example Implementations 1-18, or any combination of preceding example implementations, wherein the first end of the aerosol consumable device has a substantially oblong shape defining an oblong dimension and an end axis substantially bisecting the oblong dimension, and wherein the two or more crescent-shaped openings are symmetrically arranged on opposite sides of the aerosol cap and substantially aligned with the end axis.

Example Implementation 20: The aerosol consumable device of any one of Example Implementations 1-19, or any combination of preceding example implementations, wherein the mouthpiece portion further defines a perimeter surface located at the first end of the aerosol consumable device, and wherein the perimeter surface is raised above at least part of the top surface.

Example Implementation 21: An aerosol consumable device comprising at a first end, a mouthpiece portion configured for insertion into the mouth of a user for delivery of an aerosol generated by the aerosol consumable device, the mouthpiece portion having a top surface comprising one or more openings, at a second end, opposite the first end, a connecting portion configured to be attached to a controller portion of an aerosol delivery device, a liquid absorbing insert positioned within the mouthpiece portion between the first end and the second end, and an aerosol tube positioned between the second end and the liquid absorbing insert, wherein the liquid absorbing insert comprises an absorbent material and defines an internal aerosol channel, and wherein, upon a draw on the mouthpiece portion by the user, a first portion of the aerosol generated by the aerosol consumable device travels through the internal aerosol channel of the liquid absorbing insert and through the one or more openings, and wherein the aerosol tube is configured to direct accumulated droplets along an inner surface of the aerosol tube into the liquid absorbing insert.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE FIGURES

Figure 1:
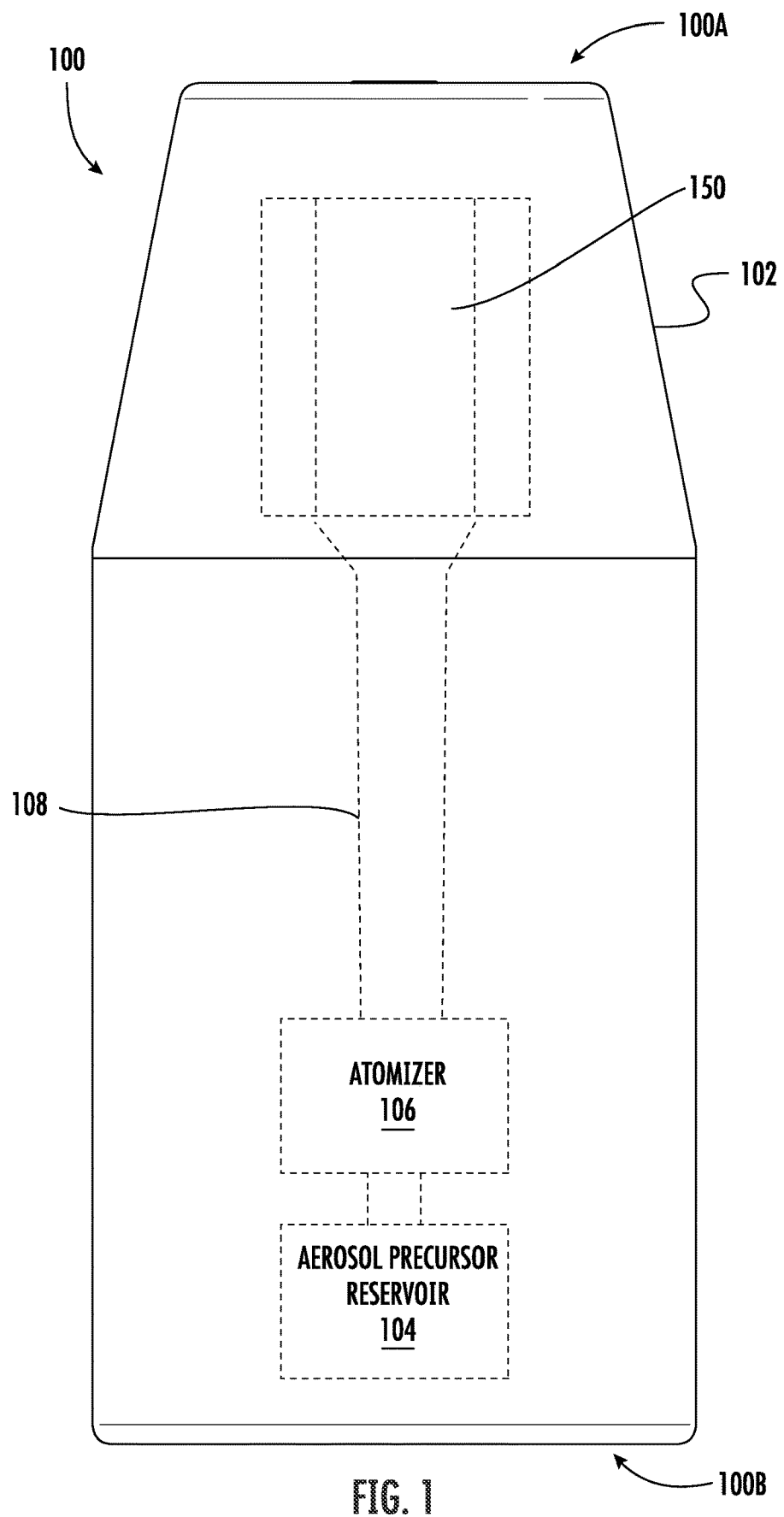
Figure 2A:
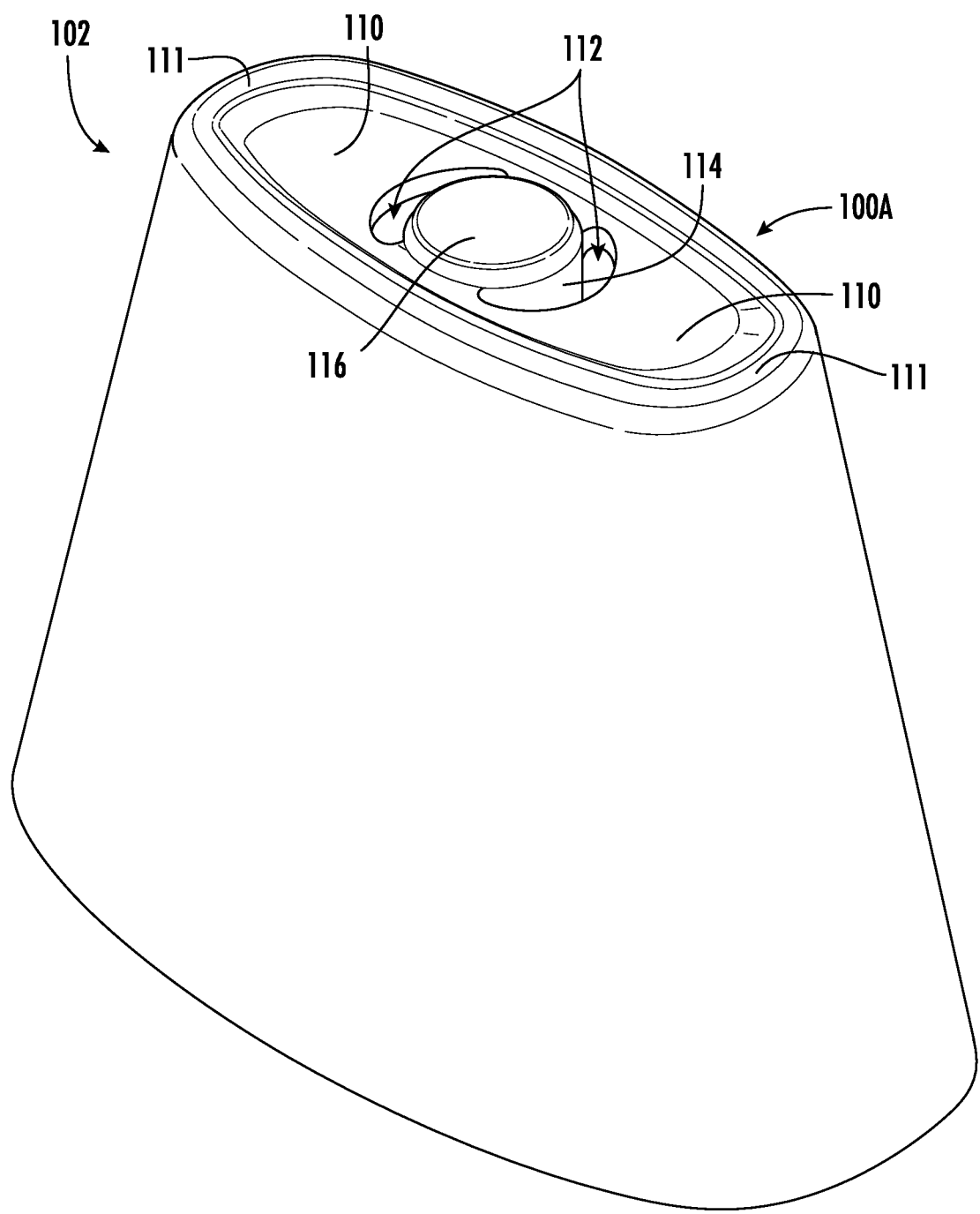
Figure 2B:
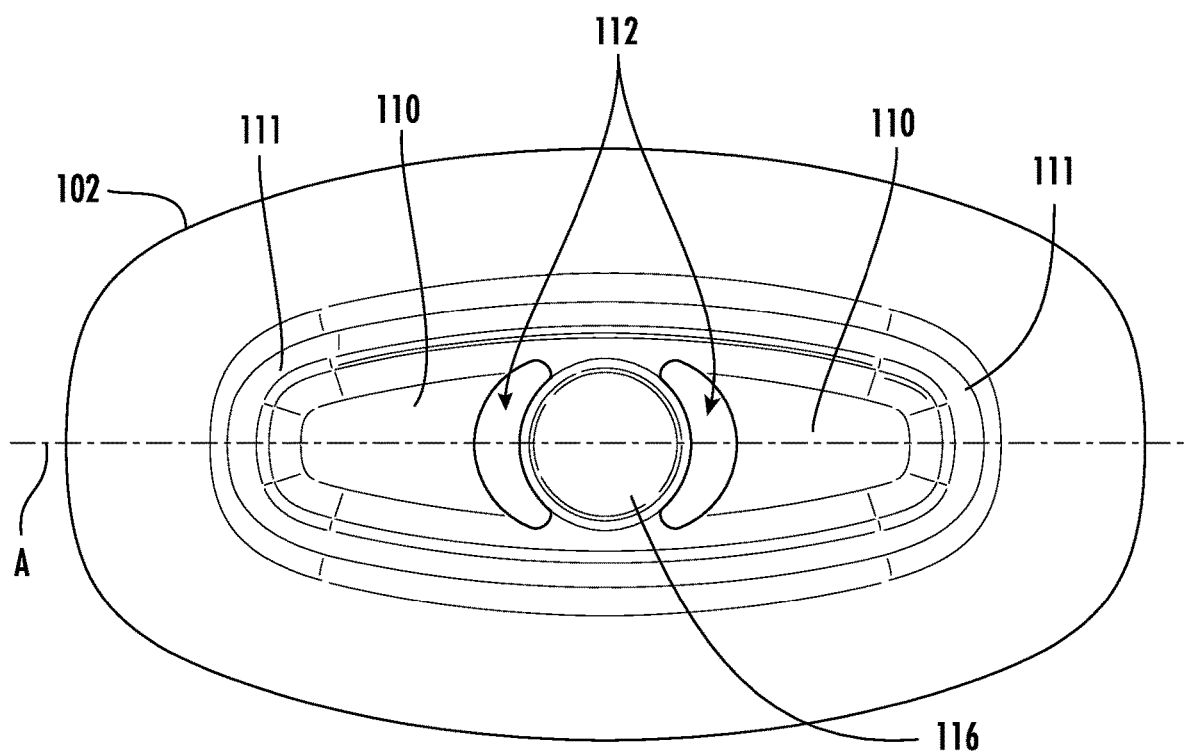
Figure 3A:
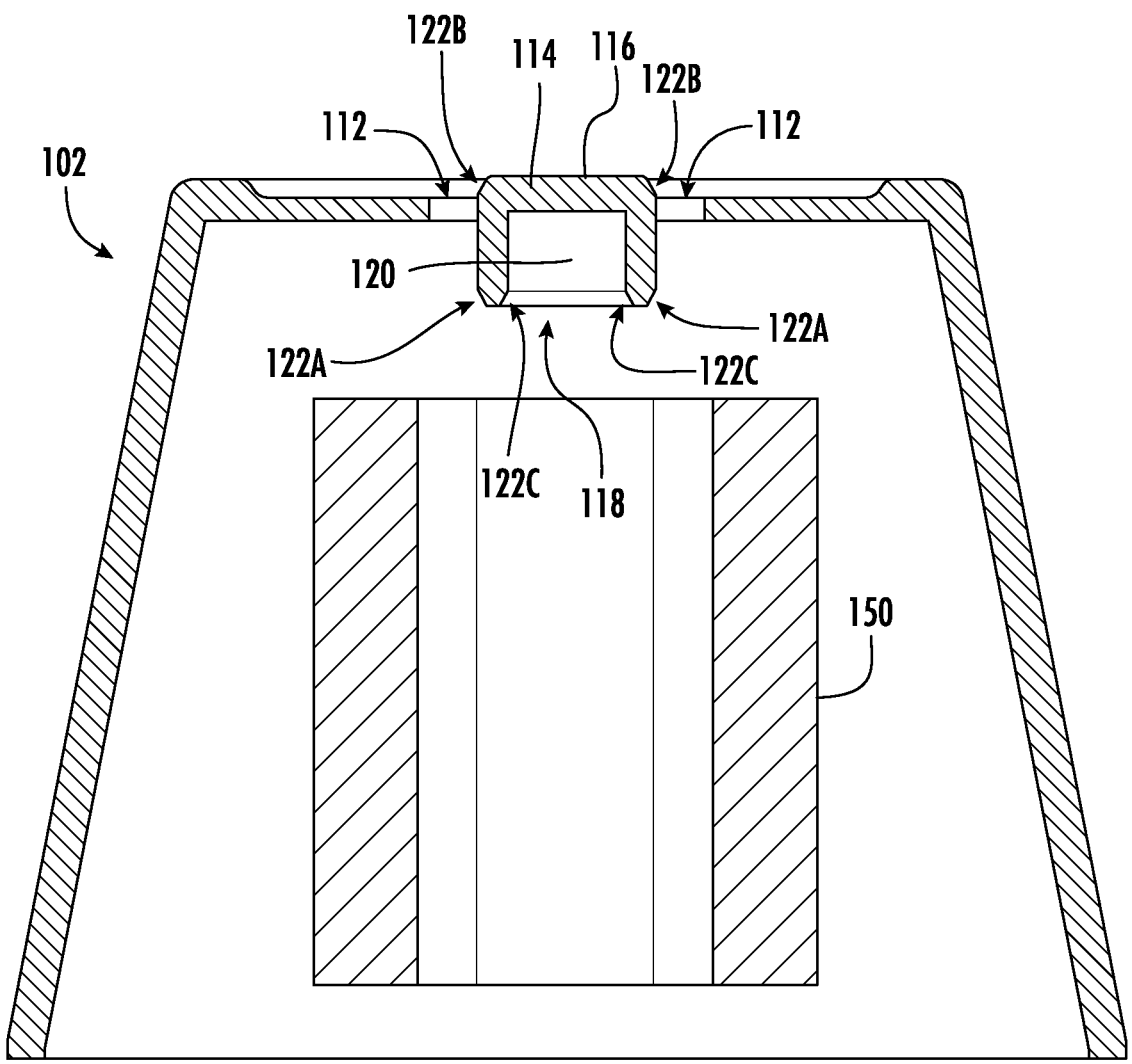
Figure 3B:
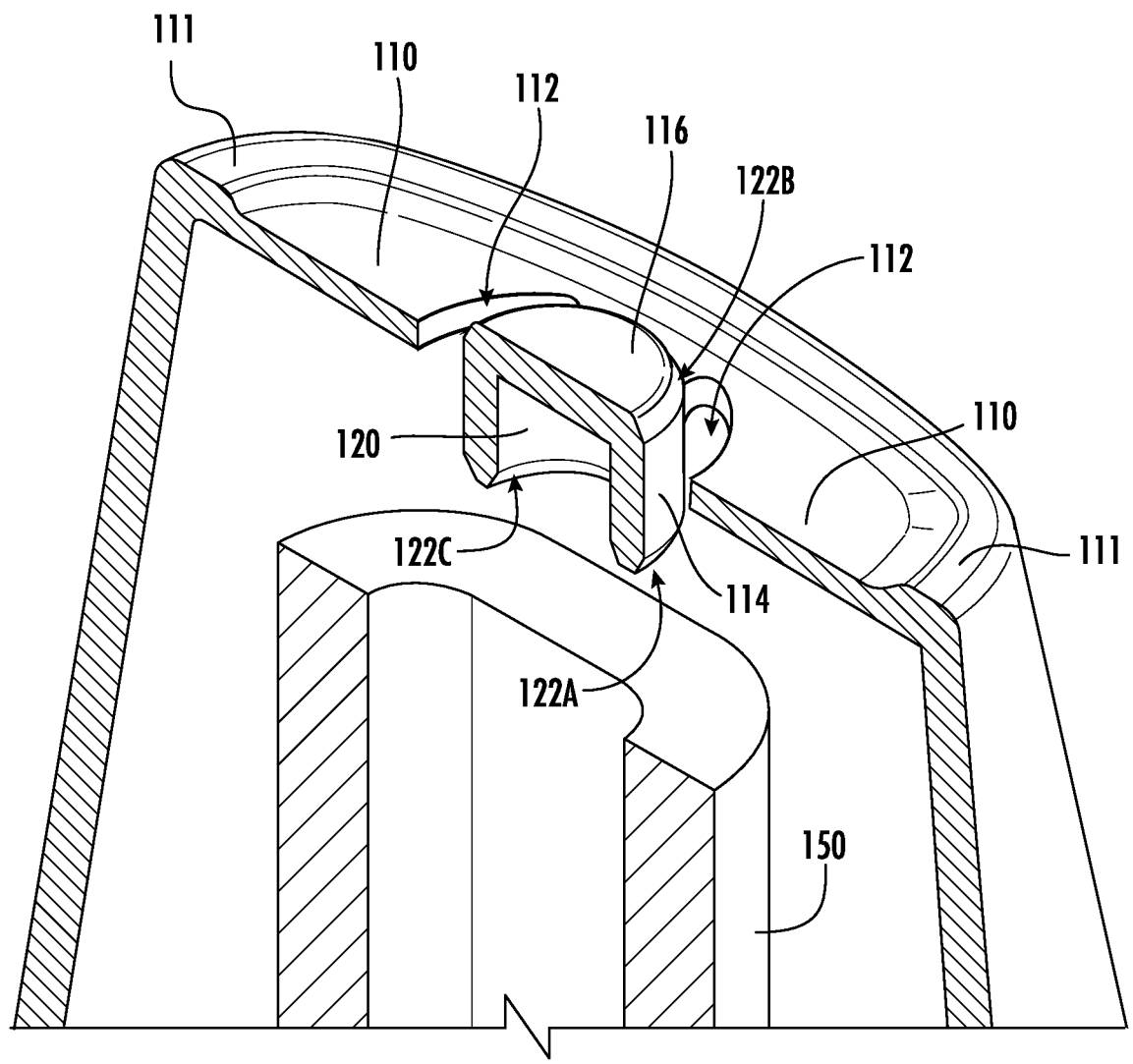
Figure 4:
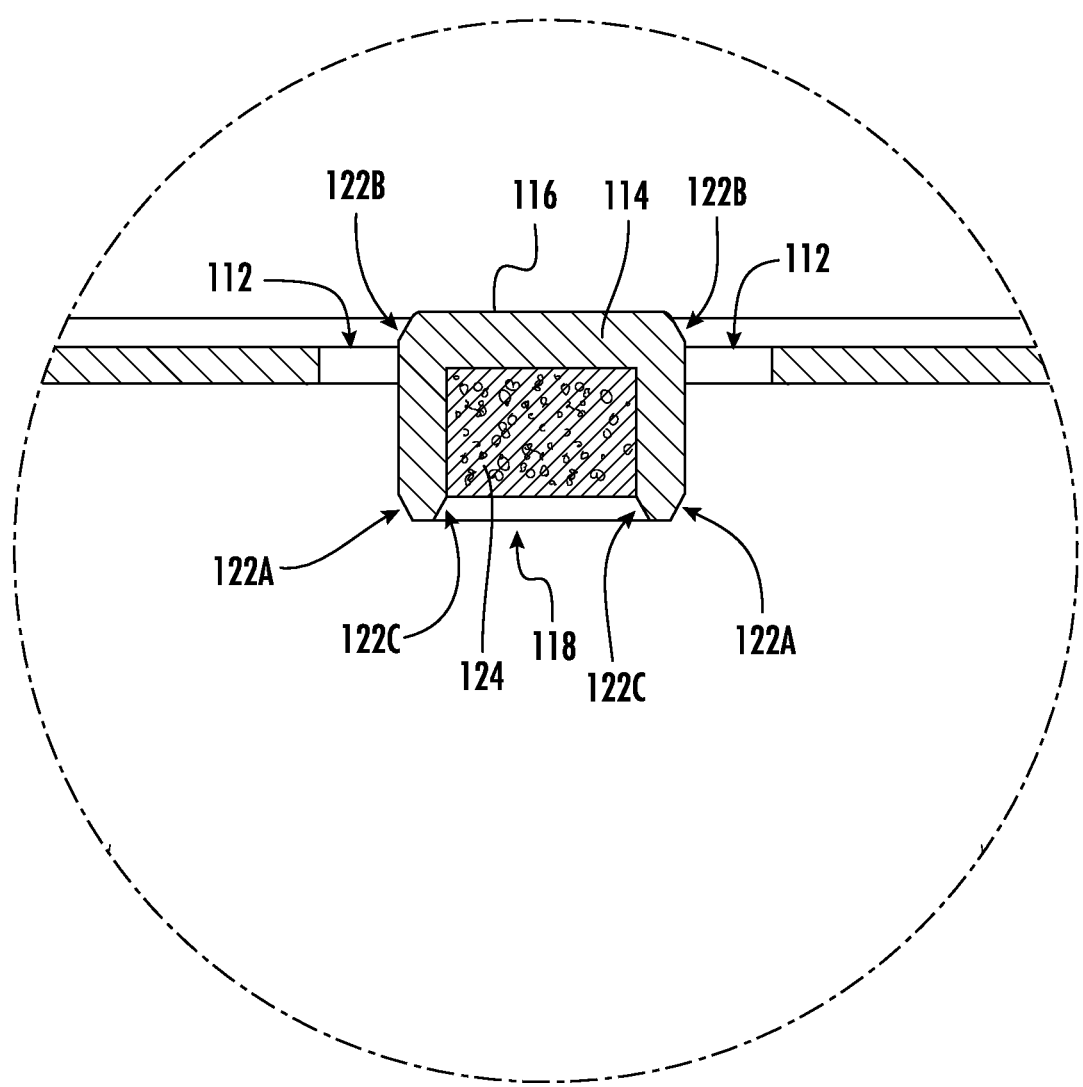
Figure 5A:
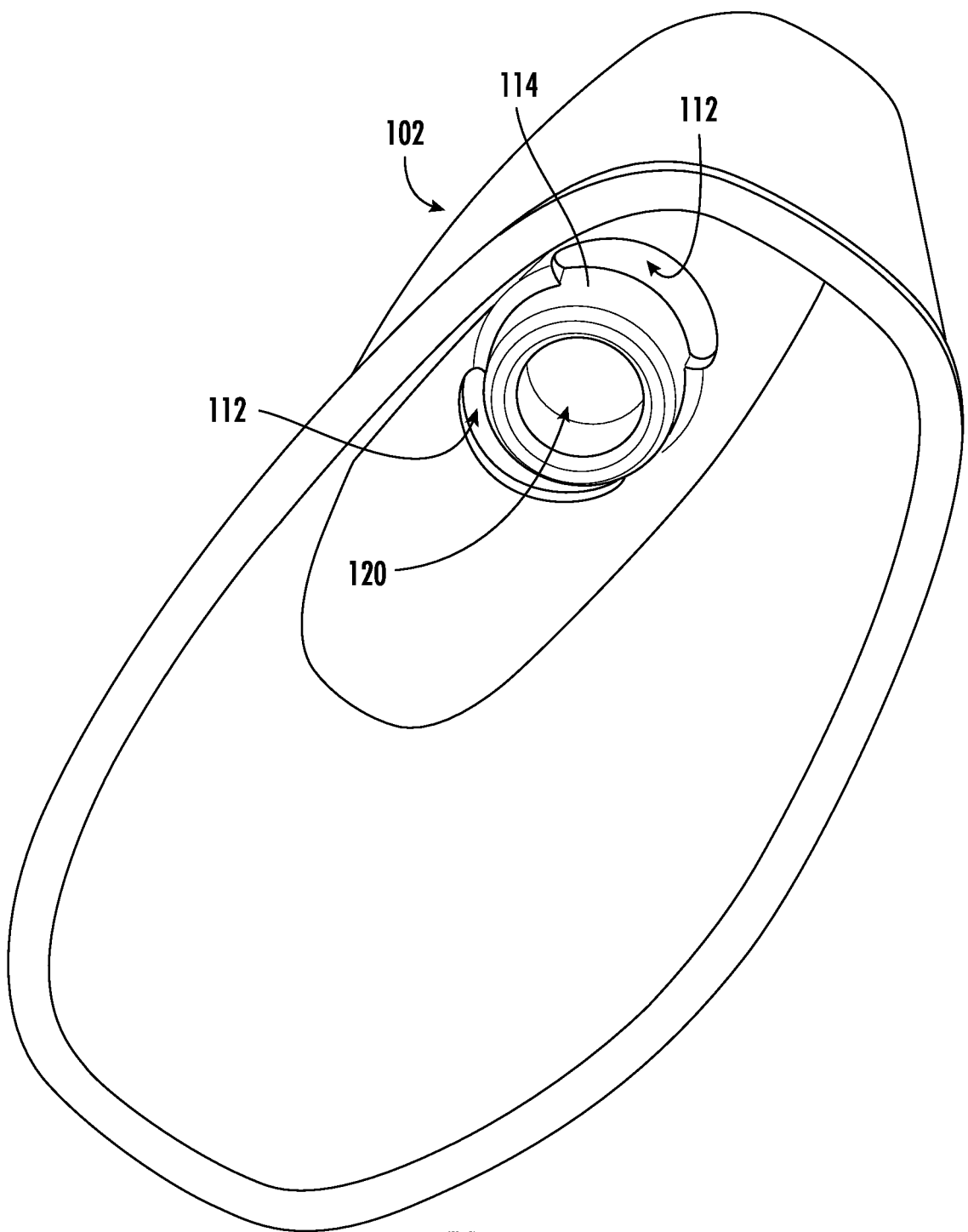
Figure 5B:
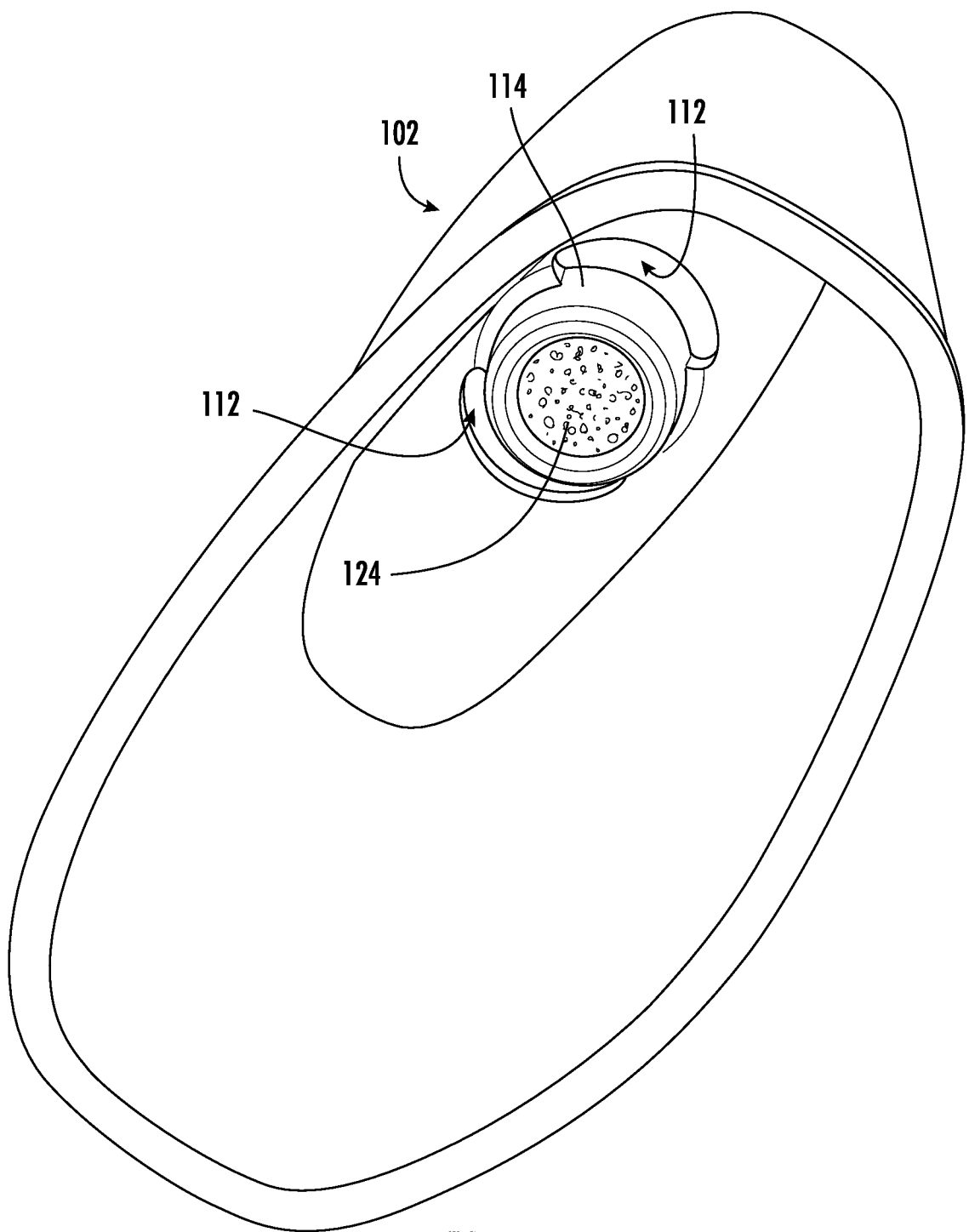
Figure 5C:
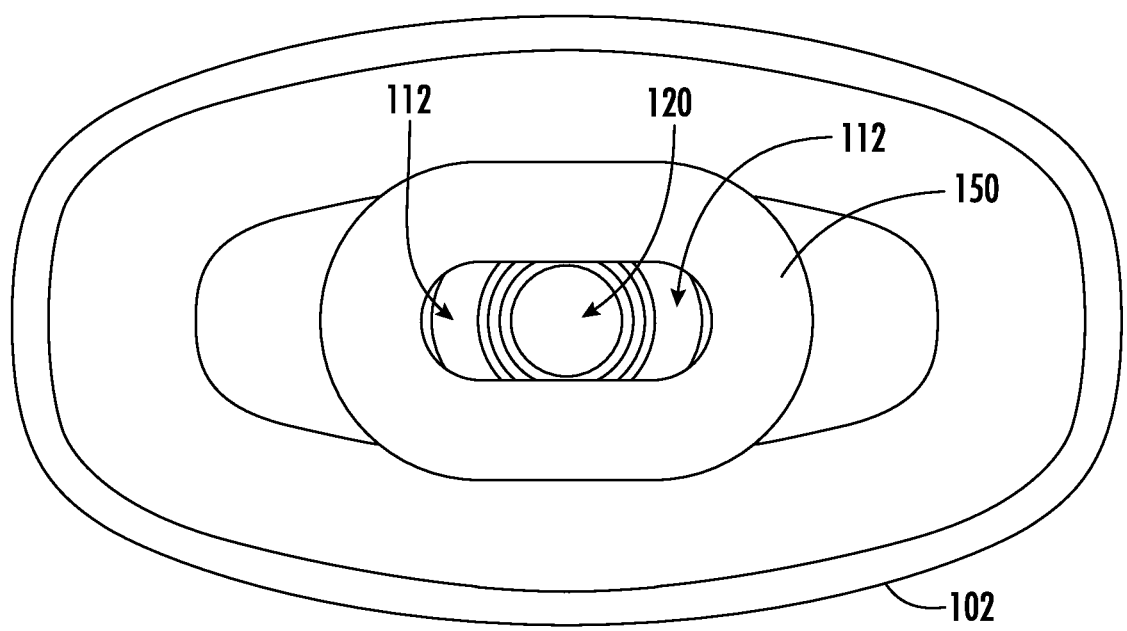
Figure 7:
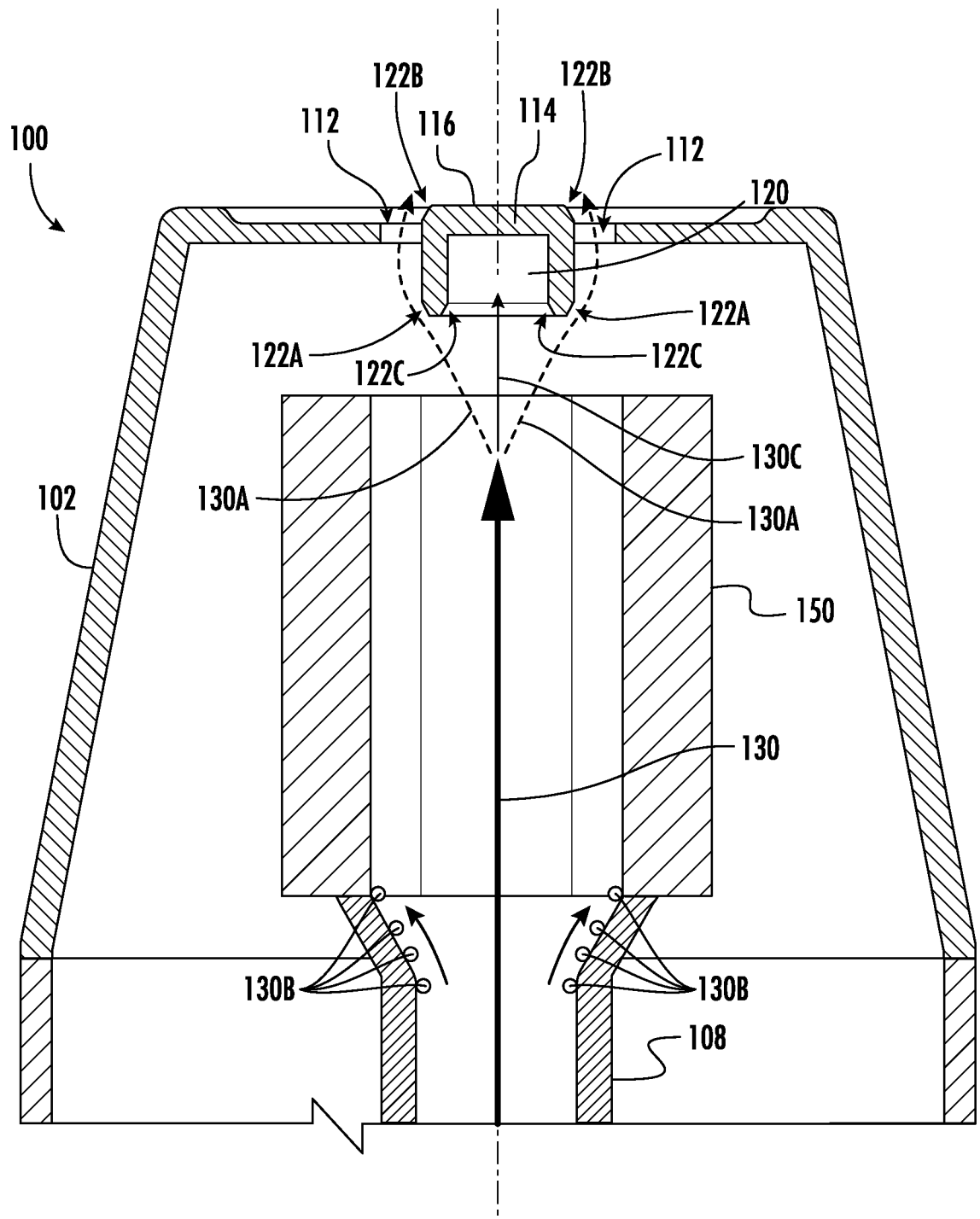

Having thus described the disclosure in the foregoing general terms, reference will now be made to the accompanying drawings, which are not necessarily drawn to scale, and wherein:

FIG. 1 is a front schematic view of an aerosol delivery device consumable, according to an example implementation of the present disclosure;

FIG. 2A is a perspective view of a mouthpiece portion of the aerosol delivery device consumable, FIG. 2B is a top view of the mouthpiece portion, according to an example implementation of the present disclosure;

FIG. 3A is a cross-sectional view of a mouthpiece portion and FIG. 3B is a perspective cross-sectional view of the mouthpiece portion, according to an example implementation of the present disclosure;

FIG. 4 is a zoomed-in cross-sectional view of a mouthpiece portion with a plug in the cavity of an aerosol cap, according to an example implementation of the present disclosure;

FIG. 5A and FIG. 5B are bottom perspective views and FIG. 5C is a bottom view of a mouthpiece portion, according to an example implementation of the present disclosure;

FIG. 6 is a front plan view of the aerosol delivery device consumable with the mouthpiece portion removed, according to some embodiments of the present disclosure; and FIG. 7 is a cross-sectional view of the aerosol delivery device consumable having a tube extending up to a liquid absorbing insert of the aerosol delivery device consumable, according to an example implementation of the present disclosure.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As described hereinafter, implementations of the present disclosure relate to aerosol delivery devices or vaporization devices, said terms being used herein interchangeably. Aerosol delivery devices according to the present disclosure use electrical energy and/or an ignitable heat source to vaporize and/or aerosolize a material to form an inhalable substance; and components of such devices have the form of articles that most preferably are sufficiently compact to be considered hand-held devices. In some embodiments, the present aerosol delivery devices may be configured to heat a material (preferably without combusting the material to any significant degree and/or without significant chemical alteration of the material) to form the inhalable substance. Preferably, use of components of preferred aerosol delivery devices does not result in the production of smoke—i.e., from by-products of combustion or pyrolysis of tobacco, but rather, use of those preferred systems results in the production of vapors resulting from volatilization or vaporization of certain components incorporated therein. In some implementations, components of aerosol delivery devices may be characterized as electronic cigarettes, and those electronic cigarettes most preferably incorporate tobacco and/or components derived from tobacco, and hence deliver tobacco derived components in aerosol form.

As noted, some implementations of aerosol delivery devices according to the present disclosure use electrical energy to energize a material to form an inhalable substance. For example, some implementations of aerosol delivery device according to the present disclosure use electrical energy to heat a material to form an inhalable substance (e.g., electrically heated tobacco products), and other implementations of aerosol delivery devices according to the present disclosure use electrical energy to vibrate a material to form an inhalable substance. Still other implementations of aerosol source members according to the present disclosure use an ignitable heat source to heat a material to form an inhalable substance (e.g., carbon heated tobacco products). The material may be heated without combusting the material to any significant degree. As such, the presently disclosed subject matter may be used in relation to a variety of aerosol and/or vapor producing devices, which may include, but is not limited to, devices commonly known as e-cigarettes, heat-not-burn (HNB) devices, carbon tobacco heated products, and electric tobacco heated products. Non-limiting examples of such devices to which any part or all of the present disclosure may be incorporated are described in U.S. Pat. Nos. 9,839,238, 9,913,493, 10,085,485, and 10,349,674, each of which is incorporated herein in its entirety.

Components of such systems have the form of articles that are sufficiently compact to be considered hand-held devices. That is, use of components of aerosol delivery devices does not result in the production of smoke in the sense that aerosol results principally from by-products of combustion or pyrolysis of tobacco, but rather, use of those systems results in the production of vapors resulting from volatilization or vaporization of certain components incorporated therein. In some example embodiments, components of aerosol delivery devices may be characterized as electronic cigarettes, and those electronic cigarettes may incorporate tobacco and/or components derived from tobacco, and hence deliver tobacco derived components in aerosol form.

Aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating device of the present disclosure can hold and use that piece much like a smoker employs a traditional type of smoking article, draw on one end of that piece for inhalation of aerosol produced by that piece, take or draw puffs at selected intervals of time, and the like.

Aerosol delivery devices of the present disclosure can also be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Some aerosol delivery devices of the present disclosure comprise some combination of a power source (i.e., an electrical power source), at least one control component (e.g., means for actuating, controlling, regulating and ceasing power for heat generation, such as by controlling electrical current flow from the power source to other components of the article—e.g., a microcontroller or microprocessor), an atomizer, a liquid composition (e.g., commonly an aerosol precursor composition liquid capable of yielding an aerosol upon application of sufficient heat, such as ingredients commonly referred to as "smoke juice," "e-liquid" and "e-juice"), and a mouthpiece or mouth portion for allowing draw upon the aerosol delivery device for aerosol inhalation (e.g., a defined airflow path through the article such that aerosol generated can be withdrawn therefrom upon draw). More specific formats, configurations and arrangements of components within the aerosol delivery devices of the present disclosure will be evident in light of the further disclosure provided hereinafter. Additionally, the selection and arrangement of various aerosol delivery device components can be appreciated upon consideration of the commercially available electronic aerosol delivery devices, such as those representative products referenced in the background art section of the present disclosure.

An example implementation of an aerosol delivery device consumable 100 of the present disclosure is illustrated in FIG. 1. In some implementations, the aerosol delivery device consumable 100 can be referred to as a "mouthpiece." As illustrated, the aerosol delivery device consumable 100 has a first end 100A and a second end 100B, opposite the first end 100A. At the first end 100A of the aerosol delivery device consumable 100, a mouthpiece portion 102 is provided. In some implementations, the mouthpiece portion 102 is separate from the remainder of the aerosol delivery device consumable 100 and can be attached, or otherwise secured, to the aerosol delivery device consumable 100. In some other implementations, the mouthpiece portion 102 is integrally formed with the aerosol delivery device consumable 100 to make one continuous piece. When referred to herein, the "mouthpiece" can be the mouthpiece portion 102 itself (e.g., detached and separate from the remainder of the aerosol delivery device consumable 100), the mouthpiece portion 102 when attached to the remainder of the aerosol delivery device consumable 100, or the aerosol delivery device consumable 100 as a whole when the mouthpiece portion 102 is integrally formed with the remainder of the aerosol delivery device consumable 100.

Although not pictured, in some implementations, the second end 100B of the aerosol delivery device consumable 100 can comprise a connecting portion configured such that the aerosol delivery device consumable 100 can be attached or connected (such as, for example, via one or more of a snap fit, interference fit, screw connection, magnetic connection, etc.) to a control unit of an aerosol delivery device such that the aerosol delivery device consumable 100 is mechanically and electrically connected to the control unit. In some instances, the combination of the aerosol delivery device consumable 100 (e.g., including the mouthpiece portion 102) with the control unit can be termed an aerosol delivery device. In other words, in some implementations, the connection of the control unit with the depicted aerosol delivery device consumable 100 creates an aerosol delivery device. In some other implementations, the aerosol delivery device consumable 100 may itself comprise an aerosol delivery device such that it can operate on its own to create an aerosol for a user without the need to be connected to another component. Those having ordinary skill in the art will appreciate that various configurations of the devices can result in an aerosol being delivered to the user.

In various implementations, the control unit may include a power source, such as a battery and/or a capacitor. For example, in some implementations the control unit may have a replaceable battery or a rechargeable battery and thus may be combined with any type of recharging technology, including connection to a wall charger, connection to a car charger (e.g., cigarette lighter receptacle, USB port, etc.), connection to a computer, any of which may include a universal serial bus (USB) cable or connector (e.g., USB 2.0, 3.0, 3.1, USB Type-C), connection to a USB connector (e.g., USB 2.0, 3.0, 3.1, USB Type-C as may be implemented in a wall outlet, electronic device, vehicle, etc.), connection to a photovoltaic cell (sometimes referred to as a solar cell) or solar panel of solar cells, or wireless charger, such as a charger that uses inductive wireless charging (including for example, wireless charging according to the Qi wireless charging standard from the Wireless Power Consortium (WPC)), or a wireless radio frequency (RF) based charger, and connection to an array of external cell(s) such as a power bank to charge a device via a USB connector or a wireless charger. An example of an inductive wireless charging system is described in U.S. Pat. App. Pub. No. 2017/0112196 to Sur et al., which is incorporated herein by reference in its entirety. In further implementations, a power source may also comprise a capacitor. Capacitors are capable of discharging more quickly than batteries and can be charged between puffs, allowing the battery to discharge into the capacitor at a lower rate than if it were used to power the heating member directly. For example, a supercapacitor—e.g., an electric double-layer capacitor (EDLC) —may be used separate from or in combination with a battery. When used alone, the supercapacitor may be recharged before each use of the article. Thus, the device may also include a charger component that can be attached to the smoking article between uses to replenish the supercapacitor. Examples of power supplies that include supercapacitors are described in U.S. Pat. App. Pub. No. 2017/0112191 to Sur et al., which is incorporated herein by reference in its entirety. Some other examples of batteries that can be used according to the disclosure are described in U.S. Pat. Pub. No. 2010/0028766 to Peckerar et al., the disclosure of which is incorporated herein by reference.

In various implementations, a draw on the device causes the battery to deliver power to an atomizer located in the aerosol precursor consumable 100. In the absence of a pressure or airflow sensor, the atomizer of some implementations may be activated manually, such as via one or more push buttons. Additional examples of sensing or detection mechanisms, structures, configurations thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; each of which is incorporated herein by reference in its entirety.

In various implementations, the control unit may also include at least one control component. In some implementations, the control component may be located on a printed circuit board (PCB), and the battery may be positioned within a body frame of the control unit. In some implementations, the control unit may also include an external connection element, such as, for example, a plurality of electrical connectors. In some implementations, the control unit may include an output element configured to provide visually perceptible output signal, such as, for example, a light source that may comprise, for example, one or more light emitting diodes (LEDs) capable of providing one or more colors of lighting. In some implementations, the light source may be positioned directly on the PCB that contains the control component. In various implementations, the PCB may include further control components (e.g., a microcontroller and/or memory components). The control unit may further include electrical pins that are positioned in a receiving chamber for forming an electrical connection with an aerosol delivery device consumable upon insertion of the consumable into the receiving chamber.

In general, the depicted implementation in FIG. 1 includes an aerosol delivery device consumable 100 that comprises a mouthpiece portion 102, an aerosol precursor reservoir 104, and an atomizer 106 configured to aerosolize a liquid composition stored in the aerosol precursor reservoir 104. The aerosol delivery device consumable 100 further comprises an aerosol tube 108 configured to provide a passageway for aerosol generated by the atomizer 106 to travel to the mouthpiece portion 102 for inhalation by a user of the aerosol delivery device consumable 100. As shown in the figure, the aerosol tube 108 comprises a first end that is attached to, or otherwise is in fluid communication with, the atomizer 106 so as to receive aerosol generated by the atomizer 106.

In the depicted implementation, the aerosol precursor reservoir 104 is configured to contain a liquid composition for vaporization—i.e., an e-liquid or aerosol precursor composition, which may be configured as otherwise described herein. The liquid composition, sometimes referred to as an aerosol precursor composition or a vapor precursor composition or "e-liquid", may comprise a variety of components, which may include, by way of example, a polyhydric alcohol (e.g., glycerin, propylene glycol, or a mixture thereof), nicotine, tobacco, tobacco extract, and/or flavorants. Representative types of aerosol precursor components and formulations are also set forth and characterized in U.S. Pat. No. 7,217,320 to Robinson et al. and U.S. Pat. App. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference in their entireties. Other aerosol precursors that may be employed include the aerosol precursors that have been incorporated in VUSE® products by R. J. Reynolds Vapor Company, the BLU™ products by Fontem Ventures B.V., the MISTIC MENTHOL product by Mistic Ecigs, MARK TEN products by Nu Mark LLC, the JUUL product by Juul Labs, Inc., and VYPE products by CN Creative Ltd. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

The amount of aerosol precursor composition that is incorporated within the aerosol delivery system is such that the aerosol generating device provides acceptable sensory and desirable performance characteristics. For example, sufficient amounts of aerosol forming material (e.g., glycerin and/or propylene glycol) may be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating device. In one or more embodiments, about 1 ml or more, about 2 ml or more, about 5 ml or more, or about 10 ml or more of the aerosol precursor composition may be included.

In the some of the examples described above, the aerosol precursor composition comprises a glycerol-based liquid. In other implementations, however, the aerosol precursor composition may be a water-based liquid. In some implementations, the water-based liquid may be comprised of more than approximately 80% water. For example, in some implementations the percentage of water in the water-based liquid may be in the inclusive range of approximately 90% to approximately 93%. In some implementations, the water-based liquid may include up to approximately 10% propylene glycol. For example, in some implementations the percentage of propylene glycol in the water-based liquid may be in the inclusive range of approximately 4% to approximately 5%. In some implementations, the water-based liquid may include up to approximately 10% flavorant. For example, in some implementations the percentage of flavorant(s) of the water-based liquid may be in the inclusive range of approximately 3% to approximately 7%. In some implementations, the water-based liquid may include up to approximately 1% nicotine. For example, in some implementations the percentage nicotine in the water-based liquid may be in the inclusive range of approximately 0.1% to approximately 1%. In some implementations, the water-based liquid may include up to approximately 10% cyclodextrin. For example, in some implementations the percentage cyclodextrin in the water-based liquid may be in the inclusive range of approximately 3% to 5%. In still other implementations, the aerosol precursor composition may be a combination of a glycerol-based liquid and a water-based liquid. For example, some implementations may include up to approximately 50% water and less than approximately 20% glycerol. The remaining components may include one or more of propylene glycol, flavorants, nicotine, cyclodextrin, etc. Some examples of water-based liquid compositions that may be suitable are disclosed in GB 1817863.2, filed Nov. 1, 2018, titled Aerosolisable Formulation; GB 1817864.0, filed Nov. 1, 2018, titled Aerosolisable Formulation; GB 1817867.3, filed Nov. 1, 2018, titled Aerosolisable Formulation; GB 1817865.7, filed Nov. 1, 2018, titled Aerosolisable Formulation; GB 1817859.0, filed Nov. 1, 2018, titled Aerosolisable Formulation; GB 1817866.5, filed Nov. 1, 2018, titled Aerosolisable Formulation; GB 1817861.6, filed Nov. 1, 2018, titled Gel and Crystalline Powder; GB 1817862.4, filed Nov. 1, 2018, titled Aerosolisable Formulation; GB 1817868.1, filed Nov. 1, 2018, titled Aerosolised Formulation; and GB 1817860.8, filed Nov. 1, 2018, titled Aerosolised Formulation, each of which is incorporated by reference herein in its entirety.

In some implementations, the aerosol precursor composition may incorporate nicotine, which may be present in various concentrations. The source of nicotine may vary, and the nicotine incorporated in the aerosol precursor composition may derive from a single source or a combination of two or more sources. For example, in some implementations the aerosol precursor composition may include nicotine derived from tobacco. In other implementations, the aerosol precursor composition may include nicotine derived from other organic plant sources, such as, for example, non-tobacco plant sources including plants in the Solanaceae family. In other implementations, the aerosol precursor composition may include synthetic nicotine. In some implementations, nicotine incorporated in the aerosol precursor composition may be derived from non-tobacco plant sources, such as other members of the Solanaceae family. The aerosol precursor composition may additionally or alternatively include other active ingredients including, but not limited to, botanical ingredients (e.g., lavender, peppermint, chamomile, basil, rosemary, thyme, eucalyptus, ginger, cannabis, ginseng, maca, and tisanes), melatonin, stimulants (e.g., caffeine, theine, and guarana), amino acids (e.g., taurine, theanine, phenylalanine, tyrosine, and tryptophan) and/or pharmaceutical, nutraceutical, nootropic, psychoactive, and medicinal ingredients (e.g., vitamins, such as B6, B12, and C and cannabinoids, such as tetrahydrocannabinol (THC) and cannabidiol (CBD)). It should be noted that the aerosol precursor composition may comprise any constituents, derivatives, or combinations of any of the above.

As noted herein, the aerosol precursor composition may comprise or be derived from one or more botanicals or constituents, derivatives, or extracts thereof. As used herein, the term "botanical" includes any material derived from plants including, but not limited to, extracts, leaves, bark, fibres, stems, roots, seeds, flowers, fruits, pollen, husk, shells or the like. Alternatively, the material may comprise an active compound naturally existing in a botanical, obtained synthetically. The material may be in the form of liquid, gas, solid, powder, dust, crushed particles, granules, pellets, shreds, strips, sheets, or the like. Example botanicals are tobacco, eucalyptus, star anise, hemp, cocoa, cannabis, fennel, lemongrass, peppermint, spearmint, rooibos, chamomile, flax, ginger, *Ginkgo biloba*, hazel, hibiscus, laurel, licorice (liquorice), matcha, mate, orange skin, papaya, rose, sage, tea such as green tea or black tea, thyme, clove, cinnamon, coffee, aniseed (anise), basil, bay leaves, cardamom, coriander, cumin, nutmeg, oregano, paprika, rosemary, saffron, lavender, lemon peel, mint, juniper, elderflower, vanilla, wintergreen, beefsteak plant, curcuma, turmeric, sandalwood, cilantro, bergamot, orange blossom, myrtle, cassis, valerian, pimento, mace, damien, marjoram, olive, lemon balm, lemon basil, chive, carvi, verbena, tarragon, geranium, mulberry, ginseng, theanine, theacrine, maca, ashwagandha, damiana, guarana, chlorophyll, baobab or any combination thereof. The mint may be chosen from the following mint varieties: Mentha Arventis, *Mentha* c.v., *Mentha niliaca, Mentha piperita, Mentha piperita citrata* c.v., *Mentha piperita* c.v, *Mentha spicata crispa, Mentha cardifolia, Mentha longifolia, Mentha suaveolens variegata, Mentha pulegium, Mentha spicata* c.v. and *Mentha suaveolens.*

As noted above, in various implementations, the aerosol precursor composition may include a flavorant or materials that alter the sensory or organoleptic character or nature of the aerosol of the smoking article. In some implementations, the flavorant may be pre-mixed with the liquid. In other implementations, the flavorant may be delivered separately downstream from the atomizer as a main or secondary flavor. Still other implementations may combine a pre-mixed flavorant with a downstream flavorant. As used herein, reference to a "flavorant" refers to compounds or components that can be aerosolized and delivered to a user and which impart a sensory experience in terms of taste and/or aroma. Example flavorants include, but are not limited to, vanillin, ethyl vanillin, cream, tea, coffee, fruit (e.g., apple, cherry, strawberry, peach and citrus flavors, including lime, lemon, mango, and other citrus flavors), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, amaretto, mojito, yerba santa, ginseng, chamomile, turmeric, *Bacopa monniera*, gingko biloba, *Withania somnifera*, cinnamon, sandalwood, jasmine, cascarilla, cocoa, licorice, and flavorings and flavor packages of the type and character traditionally used for the flavoring of cigarette, cigar, and pipe tobaccos. Other examples include flavorants derived from, or simulating, burley, oriental tobacco, flue cured tobacco, etc. Syrups, such as high fructose corn syrup, also can be employed.

Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products.

See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be noted that reference to a flavorant should not be limited to any single flavorant as described above, and may, in fact, represent a combination of one or more flavorants.

As used herein, the terms "flavor," "flavorant," "flavoring agents," etc. refer to materials which, where local regulations permit, may be used to create a desired taste, aroma, or other somatosensorial sensation in a product for adult consumers. They may include naturally occurring flavor materials, botanicals, extracts of botanicals, synthetically obtained materials, or combinations thereof (e.g., tobacco, cannabis, licorice (liquorice), hydrangea, eugenol, Japanese white bark magnolia leaf, chamomile, fenugreek, clove, maple, matcha, menthol, Japanese mint, aniseed (anise), cinnamon, turmeric, Indian spices, Asian spices, herb, wintergreen, cherry, berry, red berry, cranberry, peach, apple, orange, mango, clementine, lemon, lime, tropical fruit, papaya, rhubarb, grape, durian, dragon fruit, cucumber, blueberry, mulberry, citrus fruits, Drambuie, bourbon, scotch, whiskey, gin, tequila, rum, spearmint, peppermint, lavender, aloe vera, cardamom, celery, cascarilla, nutmeg, sandalwood, bergamot, geranium, khat, naswar, betel, shisha, pine, honey essence, rose oil, vanilla, lemon oil, orange oil, orange blossom, cherry blossom, cassia, caraway, cognac, jasmine, ylang-ylang, sage, fennel, wasabi, piment, ginger, coriander, coffee, hemp, a mint oil from any species of the genus *Mentha*, eucalyptus, star anise, cocoa, lemongrass, rooibos, flax, *Ginkgo biloba*, hazel, hibiscus, laurel, mate, orange skin, rose, tea such as green tea or black tea, thyme, juniper, elderflower, basil, bay leaves, cumin, oregano, paprika, rosemary, saffron, lemon peel, mint, beefsteak plant, curcuma, cilantro, myrtle, cassis, valerian, pimento, mace, damien, marjoram, olive, lemon balm, lemon basil, chive, carvi, verbena, tarragon, limonene, thymol, camphene), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, liquid such as an oil, solid such as a powder, or gas.

In some implementations, the flavor comprises menthol, spearmint and/or peppermint. In some embodiments, the flavor comprises flavor components of cucumber, blueberry, citrus fruits and/or redberry. In some embodiments, the flavor comprises eugenol. In some embodiments, the flavor comprises flavor components extracted from tobacco. In some embodiments, the flavor comprises flavor components extracted from cannabis.

In some implementations, the flavor may comprise a sensate, which is intended to achieve a somatosensorial sensation which are usually chemically induced and perceived by the stimulation of the fifth cranial nerve (trigeminal nerve), in addition to or in place of aroma or taste nerves, and these may include agents providing heating, cooling, tingling, numbing effect. A suitable heat effect agent may be, but is not limited to, vanillyl ethyl ether and a suitable cooling agent may be, but not limited to, eucolyptol or WS-3.

The selection of such further components may be variable based upon factors such as the sensory characteristics that are desired for the smoking article, and the present disclosure is intended to encompass any such further components that are readily apparent to those skilled in the art of tobacco and tobacco-related or tobacco-derived products. See, Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties.

As noted above, in the depicted implementation, the aerosol precursor reservoir 104 is fluidly connected to the atomizer 106. In some implementations, the atomizer 106 comprises a liquid transport element and a heater, the liquid transport element defining a fluid connection between the heater and liquid in the aerosol precursor reservoir 104. In some implementations, the atomizer 106 and liquid transport element may be configured as separate elements that are fluidly connected. In other implementations, these components may be combined. Still other implementations need not include a liquid transport element.

In various implementations, a liquid transport element may be formed of one or more materials configured for transport of a liquid, such as by capillary action. In some implementations, for example, a liquid transport element may be formed of, for example, fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. The liquid transport element thus may be any material that contains an open pore network (i.e., a plurality of pores that are interconnected so that fluid may flow from one pore to another in a plurality of direction through the element). Some implementations of the present disclosure may particularly relate to the use of non-fibrous transport elements. As such, in such embodiments, fibrous transport elements can be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. Pub. Nos. 2014/0261487 to Chapman et al. and 2014/0059780 to Davis et al.; and U.S. Pub. No. 2015/0216232 to Bless et al.; which are incorporated herein by reference. Additionally, various wicking materials, and the configuration and operation of those wicking materials within certain types of electronic cigarettes, are set forth in U.S. Pat. No. 8,910,640 to Sears et al.; which is incorporated herein by reference. In some implementations, a liquid transport element can be formed partially or completely from a porous monolith, such as a porous ceramic, a porous glass, or the like. Example monolithic materials suitable for use according to embodiments of the present disclosure are described, for example, in U.S. Pat. Pub. Nos. 2014/0123989 to LaMothe and 2017/0188626 to Davis et al., the disclosures of which are incorporated herein by reference. The porous monolith can form a substantially solid wick.

As noted, in some implementations the atomizer may comprise a heater. Various implementations of materials configured to produce heat when electrical current is applied therethrough may be employed to form the heater of the depicted implementation. In some implementations, for example, the heater may comprise a wire coil. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), titanium, platinum, silver, palladium, alloys of silver and palladium, graphite and graphite-based materials (e.g., carbon-based foams and yarns). In further implementations, the heater may be formed from conductive inks, boron doped silica, and/or ceramics (e.g., positive or negative temperature coefficient ceramics). Other types of heaters may also be utilized, such as, for example, laser diodes and/or microheaters. A laser diode may be configured to deliver electromagnetic radiation at a specific wavelength or band of wavelengths that can be tuned for vaporization of the aerosol precursor composition and/or tuned for heating a liquid transport element via which the aerosol precursor composition may be provided for vaporization. The laser diode may particularly be positioned so as to deliver the electromagnetic radiation within a chamber, and the chamber may be configured to be radiation-trapping (e.g., a black body or a white body). Suitable microheaters are described in U.S. Pat. No. 8,881,737 to Collett et al., which is incorporated herein by reference. Microheaters, for example, can comprise a substrate (e.g., quartz, silica) with a heater trace thereon (e.g., a resistive element such as Ag, Pd, Ti, Pt, Pt/Ti, boron-doped silicon, or other metals or metal alloys), which may be printed or otherwise applied to the substrate. A passivating layer (e.g., aluminum oxide or silica) may be provided over the heater trace. The heater in particular may be configured to be substantially flat. Such heaters are described in U.S. Pat. Pub. No. 2016/0345633 to DePiano et al., which is incorporated herein by reference.

As noted, further types of atomizers are also encompassed by the present disclosure. For example, in some implementations, an atomizer may comprise one or more elements adapted to or configured vaporize or aerosolize (or otherwise form a fine, particulate form of) an aerosol precursor liquid without necessarily heating the liquid. For example, in some implementations the atomizer 106 may comprise a jet nebulizer assembly, which may be configured to utilize compressed air to generate an aerosol. In other implementations, the atomizer 106 may comprise an ultrasonic assembly, which may be configured to utilize the formation of ultrasonic waves within the liquid composition to generate an aerosol. In other implementations, the atomizer 106 may comprise a vibrating assembly, such as, for example, a vibrating mesh assembly, which may comprise a piezoelectric material (e.g., a piezoelectric ceramic material) affixed to and substantially surrounding a mesh plate, (e.g., a perforated plate such as a micro-perforated mesh plate) that is vibrated within the liquid composition or proximate the surface of the liquid composition to generate an aerosol. In still other implementations, the atomizer 106 may comprise a surface acoustic wave (SAW) or Raleigh wave assembly, which may utilize surface wave characteristics to generate an aerosol at the surface of the liquid composition. It should be noted that for purpose of this application, an ultrasonic assembly may be any assembly configured to create ultrasonic waves within the liquid composition. In some implementations, for example, a vibrating mesh assembly may also operate as an ultrasonic assembly. Some examples of a piezo elements are described, for example, in U.S. Pat. Pub. No. 2013/0319404 to Feriani et al. and U.S. Pat. Pub. No. 2019/0014819 to Sur, the disclosure of each of which is incorporate herein by reference in its entirety. In some implementations, a fluid connection may be made between the vibrating assembly and liquid in the aerosol precursor reservoir 104 via the liquid transport element.

As described above, in some implementations, an aerosol delivery device may include a controller or control component for controlling the amount of electric power delivered to the atomizer 106 during draw. Representative types of electronic components, structure and configuration thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. Pub. Nos. 2009/0230117 to Fernando et al., 2014/0060554 to Collet et al., and 2014/0270727 to Ampolini et al.; and U.S. Pub. No. 2015/0257445 to Henry et al.; which are incorporated herein by reference.

In some implementations, an aerosol delivery device may include an input element to allow a user to control functions of the device and/or for output of information to a user. Any component or combination of components may be utilized as an input for controlling the function of the control unit. For example, one or more pushbuttons may be used as described in U.S. Pub. No. 2015/0245658 to Worm et al., which is incorporated herein by reference. Likewise, a touchscreen may be used as described in U.S. Pub. No. 2016/0262454 to Sears et al., which is incorporated herein by reference. As a further example, components adapted for gesture recognition based on specified movements of the aerosol delivery device may be used as an input. See, for example, U.S. Pub. No. 2016/0158782 to Henry et al., which is incorporated herein by reference. In some embodiments, an input may comprise a computer or computing device, such as a smartphone or tablet. In particular, the aerosol delivery device may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. Pub. No. 2016/0007561 to Ampolini et al., the disclosure of which is incorporated herein by reference. In such embodiments, an APP or other computer program may be used in connection with a computer or other computing device to input control instructions to the aerosol delivery device, such control instructions including, for example, the ability to form an aerosol of specific composition by choosing the nicotine content and/or content of further flavors to be included, choosing the total particulate matter (TPM) provided per puff, choosing a specific heating profile to be implemented, choosing a modifiable resistance to drawn, and the like.

Further indicators (e.g., a haptic feedback component, an audio feedback component, or the like) can be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; U.S. Pat. Pub. No. 2015/0020825 to Galloway et al.; and U.S. Pat. Pub. No. 2015/0216233 to Sears et al.; which are incorporated herein by reference. It is understood that not all of the illustrated elements are required. For example, an LED may be absent or may be replaced with a different indicator, such as a vibrating indicator.

In the implementation depicted in FIG. 1, the aerosol precursor reservoir 104 includes a liquid composition configured to produce an aerosol via the atomizer 106. Although the aerosol precursor reservoir 104 is schematically shown in FIG. 1, in various implementations, the aerosol precursor reservoir 104 may have any configuration and may have any location within the aerosol delivery device such that the aerosol precursor reservoir is in fluid communication with the atomizer 106, including, for example, a location within the aerosol delivery device consumable 100 and/or a location within the control unit. In some implementations, the aerosol precursor reservoir 104 may have an annular shape located around the aerosol tube 108.

As illustrated in FIG. 1, in some implementations, the aerosol delivery device consumable 100 comprises, at the first end 100A, a mouthpiece portion 102 configured for insertion into the mouth of a user of the aerosol delivery device consumable 100 for delivery of aerosol generated by the aerosol delivery device consumable 100. As shown more clearly in FIG. 2A, the first end 100A of the aerosol delivery device consumable 100 has a top surface 110. Furthermore, the aerosol delivery device consumable 100 comprises a second end 100B, opposite the first end 100A, which in the depicted implementation is configured to be attached to a control unit, as described hereinabove.

In some embodiments, the aerosol delivery device consumable 100 comprises a liquid absorbing insert 150 positioned within the mouthpiece portion 102 between the first end 100A and the second end 100B. In some cases, the liquid absorbing insert 150 can be positioned or located between the first end 100A and the aerosol tube 108. The liquid absorbing insert 150 comprises an absorbent material and defines an internal aerosol channel, wherein, upon a draw on the mouthpiece portion 102 by a user of the aerosol delivery device consumable 100, a portion of the aerosol generated by the aerosol delivery device consumable 100 travels through the internal aerosol channel and into the mouth of a user, and a portion of accumulated droplets are absorbed by the liquid absorbing insert 150. This function will be detailed further herein. In some cases the liquid absorbing insert 150 is comprised of any suitable woven or non-woven fibrous material. For example and without limitation, in some cases, the liquid absorbing insert 150 can be comprised of cotton, cellulose acetate, polyester, or any combination thereof. In some other cases, the liquid absorbing insert can be comprised of a rigid porous material, such as, for example and without limitation, a ceramic material.

FIG. 2A is a perspective view of the mouthpiece portion 102 of the aerosol delivery device consumable 100 according to some implementations of the present disclosure. As depicted in FIG. 2A, the top surface 110 of mouthpiece portion 102 comprises a pair of crescent-shaped openings 112 arranged on opposite sides of an aerosol cap 114. In some implementations, the top surface 110 of mouthpiece portion 102 comprises two or more, or a plurality of, crescent-shaped openings 112. In some implementations, the crescent-shaped openings 112 have a shape that is at least partially defined by the shape of the aerosol cap 114. For example and without limitation, as illustrated in FIG. 2A, the aerosol cap 114 has a substantially cylindrical shape that defines a curved inner edge of the crescent-shaped openings 112. However, in other implementations, the aerosol cap 114 can have any suitable shape such as a substantially cubic shape, a substantially rectangular prism shape, a substantially pentagonal prism shape, a substantially hexagonal prism shape, a substantially octagonal shape, or any other suitable shape.

As FIG. 2B clearly illustrates, the crescent-shaped openings 112 each have a shape that is defined by both a curved inner edge and curved outer edge, where the radius of the inner edge is greater than the radius of the outer edge, and the inner and outer edges are joined by rounded ends. As noted above, the curved inner edge of the crescent-shaped openings 112 is defined by the aerosol cap 114. Those having ordinary skill in the art will appreciate that the shape of the aerosol cap 114 may alter the shape of the inner edge of the crescent-shaped openings 112 such that it may not be curved.

As noted, in the depicted implementation, each of the pair of crescent-shaped openings 112 is arranged around a peripheral outer surface of the aerosol cap 114. Although the figures of the present application depict a mouthpiece portion 102 with only a pair of crescent-shaped openings 112, in some implementations, the mouthpiece portion 102 can comprise more than two crescent-shaped openings 112 arranged around the aerosol cap 114. Additionally, in some implementations, more than one aerosol cap 114 can be included, each with aerosol cap 114 having a pair (or more) crescent-shaped openings surrounding it.

As illustrated in both FIG. 2A and FIG. 2B, the aerosol cap 114 has a closed end which defines an outer surface 116. In some implementations, the outer surface 116 of the closed end of the aerosol cap 114 is raised above at least part of the top surface 110 of the of the mouthpiece portion 102 (i.e., also referred to as the top surface of the aerosol delivery device consumable 100). As described herein, in some implementations, the aerosol cap 114 has a substantially cylindrical shape and part of the cylindrical shape, namely a portion of the aerosol cap 114 including the outer surface 116, is on the outside of the mouthpiece portion 102, while another part of the cylindrical shape of the aerosol cap 114 extends within the mouthpiece portion 102.

As will be described further hereinbelow, the pair of crescent-shaped openings 112 and the aerosol cap 114 are configured such that, upon a draw on the mouthpiece portion 102 by a user (e.g., a puff on the mouthpiece portion 102 by the user), a first portion of an aerosol generated by the aerosol delivery device consumable 100 travels through the pair of crescent-shaped openings 112 and into the mouth of the user, accumulated droplets generated by the aerosol delivery device consumable 100 are absorbed by the liquid absorbing insert 150, and a second portion of the aerosol generated by the aerosol delivery device consumable 100 is trapped by the aerosol cap 114.

As illustrated in FIG. 2A, the mouthpiece portion 102 defines a perimeter surface 111 located at the first end 100A of the mouthpiece portion 102 or aerosol delivery device consumable 100. In some implementations, the perimeter surface 111 is raised above (e.g., in the downstream direction) at least a part of the top surface 110. In other implementations, the outer surface 116 of the closed end of the aerosol cap 114 is substantially even with (e.g., at least a portion of the outer surface 116 is substantially co-planar with) a portion of the perimeter surface 111.

Referring back to FIG. 2B, in some implementations, the first end of the mouthpiece portion 102 has a substantially oblong or oval shape. In some implementations, the mouthpiece portion 102 has a rectangular shape with rounded edges and/or rounded sides. In the depicted implementation, the first end of the mouthpiece portion 102 has a substantially oblong shape defining an oblong dimension defining an end axis A substantially bisecting the oblong dimension. In the depicted implementation, the pair of crescent-shaped openings 112 are symmetrically arranged on opposite sides of the aerosol cap 114 and substantially bisected by the end axis A. In other implementations, the pair of crescent-shaped openings need not be bisected by the end axis A, and thus may be arranged around the aerosol cap 114 at different locations. For example, in some implementations the pair of crescent-shaped openings may be substantially bisected by an axis that forms an angle (such as, for example, any angle between 0° and 180°) relative to the end axis A.

FIG. 3A is a cross-sectional view of a mouthpiece portion 102 according to some implementations of the present disclosure. As illustrated in the figure, in some implementations, the aerosol cap 114 can further define an open end 118, opposite the closed end defining the outer surface 116, thereby forming a cavity 120 in the aerosol cap 114. As illustrated in FIG. 3A, the aerosol cap 114 defines a sidewall between the closed end and the open end 118. In some implementations, an outer surface of the sidewall is chamfered. As will be described in further detail hereinbelow, in some implementations, the chamfered portion 122A of the outer surface of the sidewall can be located at the open end 118 of the aerosol cap 114 and is configured to direct the first portion of the aerosol through the crescent-shaped openings 112. In some other implementations, the chamfered portion 122B of the sidewall is located at the closed end of the aerosol cap 114 and is configured to direct the first portion of the aerosol into the mouth of the user. In some other implementations, the chamfered portions 122A and 122B are located at both the closed end and the open end 118 of the aerosol cap 114, and the chamfered portions 122A and 122B are configured to direct the first portion of the aerosol out the pair of crescent-shaped openings 112 and into the mouth of the user. In still other implementations, the aerosol cap 114 defines a sidewall between the closed end 116 and the open end 118, wherein a portion of an inner surface of the sidewall is chamfered 122C to direct the second portion of the aerosol into the cavity 120.

FIG. 3B is a perspective cross-sectional view of the mouthpiece portion 102. This view gives a different perspective of how the aerosol cap 114 is positioned within the mouthpiece portion 102 and how it helps define the shape of the pair of crescent-shaped openings 112.

Also, as illustrated in FIG. 3B, the liquid absorbing insert 150, when positioned within the mouthpiece portion 102, has an oblong tube shape. The internal aerosol channel (i.e., the hollow portion of the liquid absorbing insert 150) is clearly visible in FIG. 3B. As described in more detail in FIG. 7, in some implementations a central axis defined by the liquid absorbing insert is substantially aligned with a central axis defined by the cavity 120 of the aerosol cap 114 and/or a central axis defined by the crescent shaped openings 112.

In some implementations, the cavity 120 defined in the aerosol cap 114 may be devoid of any material such that the cavity 120 is substantially hollow. In other implementations, however, the cavity 120 defined in the aerosol cap 114 may include an insert configured to fill at least a portion of the cavity 120. FIG. 4 is a cross-sectional zoomed-in view of a mouthpiece portion 102 according to some implementations of the present disclosure with a plug 124 located in the cavity 120 of the aerosol cap 114. In various implementations, the plug may be secured in the cavity 120 in a variety of different ways, including, for example, via an interference fit and/or with the use of an adhesive. In some implementations, the plug 124 can comprise any suitable absorbent material capable of absorbing droplets or liquid. In some implementations, the plug 124 can be comprised of any suitable woven or non-woven fibrous material. For example and without limitation, the plug 124 can be comprised of cotton, cellulose acetate, polyester, or any other suitable material. As described above, in some implementations, the plug 124 is configured to absorb the second portion of the aerosol generated by the aerosol delivery device consumable 100.

FIG. 5A and FIG. 5B are bottom perspective views of the mouthpiece portion 102 according to some implementations of the present disclosure. This view gives a different perspective on how the aerosol cap 114 appears and is situated within the interior of the mouthpiece portion 102. As described above, the aerosol cap 114 can be substantially cylindrical in shape where the open end 118 of the aerosol cap 114 extends within the interior of the mouthpiece portion 102. FIG. 5B illustrates the mouthpiece portion 102 of FIG. 5A, with a plug 124 included in the aerosol cap cavity 120.

FIG. 5C is a bottom view of the mouthpiece portion 102 according to some implementations of the present disclosure. This depiction also illustrates the oblong shape of the liquid absorbing insert 150.

In some implementations, the liquid absorbing insert 150 may be located in the mouthpiece portion 102 itself. In other implementations, the liquid absorbing insert 150 may be located in a separate component of an aerosol delivery device consumable 100 (such as, for example, a separate component of an aerosol delivery device consumable 100) such that, when assembled, the liquid absorbing insert 150 is located within the mouthpiece portion 102. FIG. 6 is a front plan view of the aerosol delivery device consumable 100 with the mouthpiece portion 102 removed or detached, revealing an example holder 152 for the liquid absorbing insert 150. As described above, when positioned within the mouthpiece portion 102 (i.e., within the holder 152), the liquid absorbing insert 150 has an oblong tube shape. In some implementations, the holder 152 can be used to help form the desired shape of the liquid absorbing insert 150. In other words, the liquid absorbing insert 150 of some implementations may have a substantially cylindrical outer shape when not inserted into the holder 152, but the holder 152 is configured such that, when the liquid absorbing insert 150 is inserted into the holder 152, the inner walls of the holder 152 give the liquid absorbing insert 150 the oblong shape. In some other example embodiments, the liquid absorbing insert 150 can have a shape that fits within the holder 152 without the holder 152 substantially changing or altering the shape of the insert 150.

FIG. 7 is a front cross-sectional view of the mouthpiece portion 102 connected to or integrated with an aerosol delivery device consumable 100 having an aerosol tube 108 defining a central axis substantially aligned with a central axis of the liquid absorbing insert 150 and a central axis defined by the aerosol cap 114. As described herein, the aerosol delivery device consumable 100 can be a part of an aerosol delivery device. In such implementations, the mouthpiece portion 102 is attached to or integrated with at least a part of an aerosol delivery device. In some implementations, the part of the aerosol delivery device is the aerosol delivery device consumable 100 and the aerosol delivery device consumable 100 comprises the aerosol tube 108 defining a first central axis substantially aligned with a second central axis defined by the insert 150 and a third central axis defined by the aerosol cap 114.

As illustrated in FIG. 7, the aerosol tube 108 is configured to act as a channel for the aerosol 130, channeling the aerosol 130 received from the atomizer 106. The aerosol 130 then exits the aerosol tube 108 and enters the internal aerosol channel of the liquid absorbing insert 150. As the aerosol 130 flows through the internal aerosol chamber of the liquid absorbing insert 150, a first portion 130A of the aerosol 130, at least partially directed by the chamfered edges 122A, 122B, travels through the pair of crescent-shaped openings 112 and into the mouth of a user.

In some instances, the aerosol tube 108 includes accumulated droplets 130B that may travel upward along the inner surface of the aerosol tube 108, the accumulated droplets 130B moving with the flow of the aerosol 130 as the user draws upon the mouthpiece portion 102. The aerosol tube 108 is configured to direct the accumulated droplets into the liquid absorbing insert 150 which absorbs the accumulated droplets 130B.

In some implementations, a second hollow tube is provided within the hollow region of the liquid absorbing insert 150 (i.e., where the aerosol 130 flows). In some embodiments, the second tube is the same length as the liquid absorbing insert 150, the length being measured in the direction of the arrow indicating the aerosol 130 flow. In some embodiments, the second tube has a diameter that is substantially equal to or less than the diameter of the flow tube 108 before extending outwardly at the end. In some embodiments, a first end of the second tube closest to the flow tube 108 is spaced apart from the flow tube 108 a sufficient distance so as to allow the accumulated droplets 130B to slide up to the liquid absorbing insert 150 and be absorbed. Furthermore, the first end of the second tube is spaced close enough to the flow tube 108 to act as a barrier to block accumulated droplets 130B from entering the flow path along with the rest of the aerosol 130.

In some embodiments, a second end of the second tube, opposite the first end, is positioned to allow the aerosol 130 to flow toward the plurality of crescent-shaped openings 112 and/or the cavity 120. In some cases, the second end of the second tube can be integrally formed from the top surface 110 of the mouthpiece portion 102. In some other embodiments, the second end of the second tube terminates at the top of the liquid absorbing insert 150 (i.e., end of the liquid absorbing insert 150 closest to the cavity 120. In some other embodiments, the length of the second flow tube (i.e., the distance from the first end to the second end) can be any suitable length so that the accumulated droplets 130B are blocked from entering the flow path but are still allowed to continue to the liquid absorbing insert 150 and be absorbed and the remainder of the aerosol 130 can flow toward the toward the plurality of crescent-shaped openings 112 and/or the cavity 120 as described herein.

Furthermore, in some implementations, the cavity 120, at least partially directed by the chamfered inside edge 122C of the open end of the aerosol cap 114, is configured to receive and trap a second portion 130C of the aerosol 130. While not depicted in this scenario, the plug 124 can also be included in the cavity 120 and the plug 124 will further help absorb the second portion 130C of the aerosol 130.

In some implementations, the liquid absorbing insert 150 defines a first end and a second end. The aerosol tube 108 defines a second end proximate the second end of the liquid absorbing insert 150. In some instances, the second end of the aerosol tube 108 extends outwardly such that a diameter of the second end of the aerosol tube 108 proximate the liquid absorbing insert 150 is greater than a maximum diameter of the internal aerosol channel of the liquid absorbing insert 150. In some other instances, the second end of the aerosol tube 108 extends outwardly such that a diameter of the second end of the aerosol tube 108 proximate the liquid absorbing insert 150 is substantially the same as a maximum diameter of the internal aerosol channel of the liquid absorbing insert 150. In some embodiments, the second end of the aerosol tube 108 may define an angle with respect to the inner surface thereof. In some embodiments the angle may be between approximately 0° and approximately 60° (and in some embodiments, between approximately 5° and approximately 45°) with respect to the inner surface. For example, in the depicted embodiment, the second end of the aerosol tube 108 extends outwardly at an angle of approximately 30° with respect to the inner surface.

In some instances (such as that depicted in FIG. 7), the liquid absorbing insert 150 defines a first end and a second end, wherein the first end of the liquid absorbing insert 150 is located downstream from the second end of the liquid absorbing insert 150, and wherein the open end 118 of the aerosol cap 114 is located downstream from the first end of the liquid absorbing insert 150. In some other instances, the first end of the liquid absorbing insert 150 is located proximate the open end 118 of the aerosol cap 114. In yet other instances, the first end of the liquid absorbing insert 150 is located downstream from the open end 118 of the aerosol cap 114.

Although the implementations above are described with respect to aerosolization of a liquid composition contained in an aerosol precursor reservoir, the present disclosure should not be so limited. As such, the mouthpiece portion, and various other components of the present disclosure, may be used as part of a holder configured for use with a cartridge configured to produce an aerosol from a solid or semi-solid substrate material via an ignitable heat source (e.g., a carbon-based heat source). For example, in some implementations, the heat source may comprise a combustible fuel element that incorporates a combustible carbonaceous material. In other implementations, the heat source may incorporate elements other than combustible carbonaceous materials (e.g., tobacco components, such as powdered tobaccos or tobacco extracts; flavoring agents; salts, such as sodium chloride, potassium chloride and sodium carbonate; heat stable graphite a hollow cylindrical (e.g., tube) fibers; iron oxide powder; glass filaments; powdered calcium carbonate; alumina granules; ammonia sources, such as ammonia salts; and/or binding agents, such as guar gum, ammonium alginate and sodium alginate). In other implementations, the heat source may comprise a plurality of ignitable objects, such as, for example, a plurality of ignitable beads. In other implementations, the heat source may differ in composition or relative content amounts from those listed above. For example, in some implementations different forms of carbon could be used as a heat source, such as graphite or graphene. In other implementations, the heat source may have increased levels of activated carbon, different porosities of carbon, different amounts of carbon, blends of any above mentioned components, etc. In still other implementations, the heat source may comprise a non-carbon heat source, such as, for example, a combustible liquefied gas configured to generate heat upon ignition thereof. For example, in some implementations, the liquefied gas may comprise one or more of petroleum gas (LPG or LP-gas), propane, propylene, butylenes, butane, isobutene, methyl propane, or n-butane. In still other embodiments, the heat source may comprise a chemical reaction based heat source, wherein ignition of the heat source comprises the interaction of two or more individual components. For example, a chemical reaction based heat source may comprise metallic agents and an activating solution, wherein the heat source is activated when the metallic agents and the activating solution come in contact. Some examples of chemical based heat sources can be found in U.S. Pat. No. 7,290,549 to Banerjee et al., which is incorporated herein by reference in its entirety. Combinations of heat sources are also possible.

In some implementations, the heat source may comprise a foamed carbon monolith formed in a foam process of the type disclosed in U.S. Pat. No. 7,615,184 to Lobovsky, which is incorporated herein by reference in its entirety. As such, some implementations may provide advantages with regard to reduced time taken to ignite the heat source. In some other implementations, the heat source may be co-extruded with a layer of insulation (not shown), thereby reducing manufacturing time and expense. Other implementations of fuel elements include carbon fibers of the type described in U.S. Pat. No. 4,922,901 to Brooks et al. or other heat source implementations such as is disclosed in U.S. Pat. App. Pub. No. 2009/0044818 to Takeuchi et al., each of which is incorporated herein by reference in its entirety. Further examples of heat sources including debossed heat source systems, methods, and smoking articles that include such heat sources are disclosed in U.S. patent application Ser. No. 15/902,665, filed on Feb. 22, 2018, and titled System for Debossing a Heat Generation Member, a Smoking Article Including the Debossed Heat Generation Member, and a Related Method, which is incorporated herein by reference in its entirety.

Generally, the heat source is positioned sufficiently near an aerosol delivery component, for example, a substrate material, having one or more aerosolizable components so that the aerosol formed/volatilized by the application of heat from the heat source to the aerosolizable components (as well as any flavorants, medicaments, and/or the like that are likewise provided for delivery to a user) is deliverable to the user by way of the mouthpiece portion 102. That is, when the heat source heats the substrate component, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof. Additionally, the selection of various smoking article elements are appreciated upon consideration of commercially available electronic smoking articles, such as those representative products listed in the background art section of the present disclosure.

Preferably, the elements of the substrate material do not experience thermal decomposition (e.g., charring, scorching, or burning) to any significant degree, and the aerosolized components are entrained in the air drawn through the smoking article, including a filter (if present), and into the mouth of the user.

In various implementations, the substrate material may comprise a tobacco material, a non-tobacco material, or a combination thereof. In one implementation, for example, the substrate material may comprise a blend of flavorful and aromatic tobaccos in cut filler form. In another implementation, the substrate material may comprise a reconstituted tobacco material, such as described in U.S. Pat. No. 4,807,809 to Pryor et al.; U.S. Pat. No. 4,889,143 to Pryor et al. and U.S. Pat. No. 5,025,814 to Raker, the disclosures of which are incorporated herein by reference in their entirety. Additionally, a reconstituted tobacco material may include a reconstituted tobacco paper for the type of cigarettes described in Chemical and Biological Studies on New Cigarette Prototypes that Heat Instead of Burn Tobacco, R. J. Reynolds Tobacco Company Monograph (1988), the contents of which are incorporated herein by reference in its entirety. For example, a reconstituted tobacco material may include a sheet-like material containing tobacco and/or tobacco-related materials. As such, in some implementations, the substrate material may be formed from a wound roll of a reconstituted tobacco material. In another implementation, the substrate material may be formed from shreds, strips, and/or the like of a reconstituted tobacco material. In another implementation, the tobacco sheet may comprise overlapping layers (e.g., a gathered web), which may, or may not, include heat conducting constituents. Examples of substrate portions that include a series of overlapping layers (e.g., gathered webs) of an initial substrate sheet formed by the fibrous filler material, aerosol forming material, and plurality of heat conducting constituents are described in U.S. Pat. App. Pub. No. 2019/0261685 to Sebastian et al., which is incorporated herein by reference in its entirety.

In some implementations, the substrate material may include a plurality of microcapsules, beads, granules, and/or the like having a tobacco-related material. For example, a representative microcapsule may be generally spherical in shape, and may have an outer cover or shell that contains a liquid center region of a tobacco-derived extract and/or the like. In some implementations, one or more of the substrate materials may include a plurality of microcapsules each formed into a hollow cylindrical shape. In some implementations, one or more of the substrate materials may include a binder material configured to maintain the structural shape and/or integrity of the plurality of microcapsules formed into the hollow cylindrical shape. Tobacco employed in one or more of the substrate materials may include, or may be derived from, tobaccos such as flue-cured tobacco, burley tobacco, Oriental tobacco, Maryland tobacco, dark tobacco, dark-fired tobacco and *Rustica* tobacco, as well as other rare or specialty tobaccos, or blends thereof. Various representative tobacco types, processed types of tobaccos, and types of tobacco blends are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,159,942 to Brinkley et al.; U.S. Pat. No. 5,220,930 to Gentry; U.S. Pat. No. 5,360,023 to Blakley et al.; U.S. Pat. No. 6,701,936 to Shafer et al.; U.S. Pat. No. 6,730,832 to Dominguez et al.; U.S. Pat. No. 7,011,096 to Li et al.; U.S. Pat. No. 7,017,585 to Li et al.; U.S. Pat. No. 7,025,066 to Lawson et al.; U.S. Pat. App. Pub. No. 2004/0255965 to Perfetti et al.; PCT Pub. No. WO 02/37990 to Bereman; and Bombick et al., *Fund. Appl. Toxicol.*, 39, p. 11-17 (1997); the disclosures of which are incorporated herein by reference in their entireties.

In still other implementations of the present disclosure, the substrate material may include an extruded structure that includes, or is essentially comprised of a tobacco, a tobacco related material, glycerin, water, and/or a binder material, although certain formulations may exclude the binder material. In various implementations, suitable binder materials may include alginates, such as ammonium alginate, propylene glycol alginate, potassium alginate, and sodium alginate. Alginates, and particularly high viscosity alginates, may be employed in conjunction with controlled levels of free calcium ions. Other suitable binder materials include hydroxypropylcellulose such as Klucel H from Aqualon Co.; hydroxypropylmethylcellulose such as Methocel K4MS from The Dow Chemical Co.; hydroxyethylcellulose such as Natrosol 250 MRCS from Aqualon Co.; microcrystalline cellulose such as Avicel from FMC; methylcellulose such as Methocel A4M from The Dow Chemical Co.; and sodium carboxymethyl cellulose such as CMC 7HF and CMC 7H4F from Hercules Inc. Still other possible binder materials include starches (e.g., corn starch), guar gum, carrageenan, locust bean gum, pectins and xanthan gum. In some implementations, combinations or blends of two or more binder materials may be employed. Other examples of binder materials are described, for example, in U.S. Pat. No.

5,101,839 to Jakob et al.; and U.S. Pat. No. 4,924,887 to Raker et al., each of which is incorporated herein by reference in its entirety. In some implementations, the aerosol forming material may be provided as a portion of the binder material (e.g., propylene glycol alginate). In addition, in some implementations, the binder material may comprise nanocellulose derived from a tobacco or other biomass.

In some implementations, the substrate material may include an extruded material, as described in U.S. Pat. App. Pub. No. 2012/0042885 to Stone et al., which is incorporated herein by reference in its entirety. In yet another implementation, the substrate material may include an extruded structure and/or substrate formed from marumarized and/or non-marumarized tobacco. Marumarized tobacco is known, for example, from U.S. Pat. No. 5,105,831 to Banerjee, et al., which is incorporated by reference herein in its entirety. Marumarized tobacco includes about 20 to about 50 percent (by weight) tobacco blend in powder form, with glycerol (at about 20 to about 30 percent weight), calcium carbonate (generally at about 10 to about 60 percent by weight, often at about 40 to about 60 percent by weight), along with binder agents, as described herein, and/or flavoring agents. In various implementations, the extruded material may have one or more longitudinal openings.

In various implementations, the substrate material may take on a variety of conformations based upon the various amounts of materials utilized therein. For example, a sample substrate material may comprise up to approximately 98% by weight, up to approximately 95% by weight, or up to approximately 90% by weight of a tobacco and/or tobacco related material. A sample substrate material may also comprise up to approximately 25% by weight, approximately 20% by weight, or approximately 15% by weight water—particularly approximately 2% to approximately 25%, approximately 5% to approximately 20%, or approximately 7% to approximately 15% by weight water. Flavors and the like (which include, for example, medicaments, such as nicotine) may comprise up to approximately 10%, up to about 8%, or up to about 5% by weight of the aerosol delivery component.

Additionally, or alternatively, the substrate material may include an extruded structure and/or a substrate that includes or essentially is comprised of tobacco, glycerin, water, and/or binder material, and is further configured to substantially maintain its structure throughout the aerosol-generating process. That is, the substrate material may be configured to substantially maintain its shape (e.g., the substrate material does not continually deform under an applied shear stress) throughout the aerosol-generating process. Although such an example substrate material may include liquids and/or some moisture content, the substrate may remain substantially solid throughout the aerosol-generating process and may substantially maintain structural integrity throughout the aerosol-generating process. Example tobacco and/or tobacco related materials suitable for a substantially solid substrate material are described in U.S. Pat. App. Pub. No. 2015/0157052 to Ademe et al.; U.S. Pat. App. Pub. No. 2015/0335070 to Sears et al.; U.S. Pat. No. 6,204,287 to White; and U.S. Pat. No. 5,060,676 to Hearn et al., which are incorporated herein by reference in their entirety.

In some implementations, the amount of substrate material used within the smoking article may be such that the article exhibits acceptable sensory and organoleptic properties, and desirable performance characteristics. For example, in some implementations an aerosol precursor composition such as, for example, glycerin and/or propylene glycol, may be employed within the substrate material in order to provide for the generation of a visible mainstream aerosol that in many regards resembles the appearance of tobacco smoke. For example, the amount of aerosol precursor composition incorporated into the substrate material of the smoking article may be in the range of about 3.5 grams or less, about 3 grams or less, about 2.5 grams or less, about 2 grams or less, about 1.5 grams or less, about 1 gram or less, or about 0.5 gram or less.

According to another implementation, a smoking article according to the present disclosure may include a substrate material comprising a porous, inert material such as, for example, a ceramic material. For example, in some implementations ceramics of various shapes and geometries (e.g., beads, rods, tubes, etc.) may be used, which have various pore morphology. In addition, in some implementations non-tobacco materials, such as an aerosol precursor composition, may be loaded into the ceramics. In another implementation, the substrate material may include a porous, inert material that does not substantially react, chemically and/or physically, with a tobacco-related material such as, for example, a tobacco-derived extract. In addition, an extruded tobacco, such as those described above, may be porous. For example, in some implementations an extruded tobacco material may have an inert gas, such as, for example, nitrogen, that acts as a blowing agent during the extrusion process.

As noted above, in various implementations one or more of the substrate materials may include a tobacco, a tobacco component, and/or a tobacco-derived material that has been treated, manufactured, produced, and/or processed to incorporate an aerosol precursor composition (e.g., humectants such as, for example, propylene glycol, glycerin, and/or the like) and/or at least one flavoring agent, as well as a flame/burn retardant (e.g., diammonium phosphate and/or another salt) configured to help prevent ignition, pyrolysis, combustion, and/or scorching of the substrate material by the heat source. Various manners and methods for incorporating tobacco into smoking articles, and particularly smoking articles that are designed so as to not purposefully burn virtually all of the tobacco within those smoking articles are set forth in U.S. Pat. No. 4,947,874 to Brooks et al.; U.S. Pat. No. 7,647,932 to Cantrell et al.; U.S. Pat. No. 8,079,371 to Robinson et al.; U.S. Pat. No. 7,290,549 to Banerjee et al.; and U.S. Pat. App. Pub. No. 2007/0215167 to Crooks et al.; the disclosures of which are incorporated herein by reference in their entireties.

As noted, in some implementations, flame/burn retardant materials and other additives that may be included within one or more of the substrate materials and may include organo-phosphorus compounds, borax, hydrated alumina, graphite, potassium tripolyphosphate, dipentaerythritol, pentaerythritol, and polyols. Others such as nitrogenous phosphonic acid salts, mono-ammonium phosphate, ammonium polyphosphate, ammonium bromide, ammonium borate, ethanolammonium borate, ammonium sulphamate, halogenated organic compounds, thiourea, and antimony oxides are suitable but are not preferred agents. In each aspect of flame-retardant, burn-retardant, and/or scorch-retardant materials used in the substrate material and/or other components (whether alone or in combination with each other and/or other materials), the desirable properties most preferably are provided without undesirable off-gassing or melting-type behavior.

According to other implementations of the present disclosure, the substrate material may also incorporate tobacco additives of the type that are traditionally used for the manufacture of tobacco products. Those additives may include the types of materials used to enhance the flavor and aroma of tobaccos used for the production of cigars, cigarettes, pipes, and the like. For example, those additives may include various cigarette casing and/or top dressing components. See, for example, U.S. Pat. No. 3,419,015 to Wochnowski; U.S. Pat. No. 4,054,145 to Berndt et al.; U.S. Pat. No. 4,887,619 to Burcham, Jr. et al.; U.S. Pat. No. 5,022,416 to Watson; U.S. Pat. No. 5,103,842 to Strang et al.; and U.S. Pat. No. 5,711,320 to Martin; the disclosures of which are incorporated herein by reference in their entireties. Preferred casing materials may include water, sugars and syrups (e.g., sucrose, glucose and high fructose corn syrup), humectants (e.g. glycerin or propylene glycol), and flavoring agents (e.g., cocoa and licorice). Those added components may also include top dressing materials (e.g., flavoring materials, such as menthol). See, for example, U.S. Pat. No. 4,449,541 to Mays et al., the disclosure of which is incorporated herein by reference in its entirety. Further materials that may be added include those disclosed in U.S. Pat. No. 4,830,028 to Lawson et al. and U.S. Pat. No. 8,186,360 to Marshall et al., the disclosures of which are incorporated herein by reference in their entireties.

In some implementations, the substrate material may comprise a liquid including an aerosol precursor composition and/or a gel including an aerosol precursor composition. Some examples of liquid compositions can be found in U.S. Pat. App. Pub. No. 2020/0113239 to Aller et al., which is incorporated herein by reference in its entirety.

As noted above, in various implementations, one or more of the substrate materials may have an aerosol precursor composition associated therewith. For example, in some implementations the aerosol precursor composition may comprise one or more different components, such as polyhydric alcohol (e.g., glycerin, propylene glycol, or a mixture thereof). Representative types of further aerosol precursor compositions are set forth in U.S. Pat. No. 4,793,365 to Sensabaugh, Jr. et al.; U.S. Pat. No. 5,101,839 to Jakob et al.; PCT WO 98/57556 to Biggs et al.; and Chemical and Biological Studies on New Cigarette Prototypes that Heat Instead of Burn Tobacco, R. J. Reynolds Tobacco Company Monograph (1988); the disclosures of which are incorporated herein by reference. In some aspects, a substrate material may produce a visible aerosol upon the application of sufficient heat thereto (and cooling with air, if necessary), and the substrate material may produce an aerosol that is "smoke-like." In other aspects, the substrate material may produce an aerosol that is substantially non-visible but is recognized as present by other characteristics, such as flavor or texture. Thus, the nature of the produced aerosol may be variable depending upon the specific components of the aerosol delivery component. The substrate material may be chemically simple relative to the chemical nature of the smoke produced by burning tobacco.

In some implementations, the aerosol precursor composition may incorporate nicotine, which may be present in various concentrations. The source of nicotine may vary, and the nicotine incorporated in the aerosol precursor composition may derive from a single source or a combination of two or more sources. For example, in some implementations the aerosol precursor composition may include nicotine derived from tobacco. In other implementations, the aerosol precursor composition may include nicotine derived from other organic plant sources, such as, for example, non-tobacco plant sources including plants in the Solanaceae family. In other implementations, the aerosol precursor composition may include synthetic nicotine. In some implementations, nicotine incorporated in the aerosol precursor composition may be derived from non-tobacco plant sources, such as other members of the Solanaceae family. The aerosol precursor composition may additionally, or alternatively, include other active ingredients including, but not limited to, botanical ingredients (e.g., lavender, peppermint, chamomile, basil, rosemary, thyme, eucalyptus, ginger, cannabis, ginseng, maca, and tisanes), stimulants (e.g., caffeine and guarana), amino acids (e.g., taurine, theanine, phenylalanine, tyrosine, and tryptophan) and/or pharmaceutical, nutraceutical, and medicinal ingredients (e.g., vitamins, such as B6, B12, and C and cannabinoids, such as tetrahydrocannabinol (THC) and cannabidiol (CBD)). It should be noted that the aerosol precursor composition may comprise any constituents, derivatives, or combinations of any of the above.

As noted herein, the aerosol precursor composition may comprise or be derived from one or more botanicals or constituents, derivatives, or extracts thereof. As used herein, the term "botanical" includes any material derived from plants including, but not limited to, extracts, leaves, bark, fibres, stems, roots, seeds, flowers, fruits, pollen, husk, shells or the like. Alternatively, the material may comprise an active compound naturally existing in a botanical, obtained synthetically. The material may be in the form of liquid, gas, solid, powder, dust, crushed particles, granules, pellets, shreds, strips, sheets, or the like. Example botanicals are tobacco, eucalyptus, star anise, hemp, cocoa, cannabis, fennel, lemongrass, peppermint, spearmint, rooibos, chamomile, flax, ginger, *Ginkgo biloba*, hazel, hibiscus, laurel, licorice (liquorice), matcha, mate, orange skin, papaya, rose, sage, tea such as green tea or black tea, thyme, clove, cinnamon, coffee, aniseed (anise), basil, bay leaves, cardamom, coriander, cumin, nutmeg, oregano, paprika, rosemary, saffron, lavender, lemon peel, mint, juniper, elderflower, vanilla, wintergreen, beefsteak plant, curcuma, turmeric, sandalwood, cilantro, bergamot, orange blossom, myrtle, cassis, valerian, pimento, mace, damien, marjoram, olive, lemon balm, lemon basil, chive, carvi, verbena, tarragon, geranium, mulberry, ginseng, theanine, theacrine, maca, ashwagandha, damiana, guarana, chlorophyll, baobab or any combination thereof. The mint may be chosen from the following mint varieties: Mentha Arventis, *Mentha* c.v., *Mentha niliaca, Mentha piperita, Mentha piperita citrata* c.v., *Mentha piperita* c.v, *Mentha spicata crispa, Mentha cardifolia, Mentha longifolia, Mentha suaveolens variegata, Mentha pulegium, Mentha spicata* c.v. and *Mentha suaveolens*.

A wide variety of types of flavoring agents, or materials that alter the sensory or organoleptic character or nature of the mainstream aerosol of the smoking article may be suitable to be employed. In some implementations, such flavoring agents may be provided from sources other than tobacco and may be natural or artificial in nature. Reference is made to the above description regarding possible flavorants, flavoring agents, and/or other components, which will not be duplicated here.

In one or more implementations, the present disclosure may be directed to kits that provide a variety of components as described herein. For example, a kit may comprise a control unit with one or more mouthpieces (or mouthpiece portions). A kit may further comprise a plurality of control units with a plurality of mouthpieces (or mouthpiece portions). A kit may further comprise a plurality of control units with one or more mouthpieces (or mouthpiece portions). A kit may further comprise a control unit with one or more batteries. A kit may further comprise a control unit with one or more mouthpieces (or mouthpiece portions) and one or more charging components and/or one or more batteries. A kit may further comprise a plurality of mouthpieces (or mouthpiece portions). A kit may further comprise a plurality of mouthpieces (or mouthpiece portions) and one or more batteries and/or one or more charging components. In the above implementations, the mouthpieces (or mouthpiece portions) or the control units may be provided with an atomizer inclusive thereto. The inventive kits may further include a case (or other packaging, carrying, or storage component) that accommodates one or more of the further kit components. The case could be a reusable hard or soft container. Further, the case could be simply a box or other packaging structure.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol consumable device comprising:
   at a first end, a mouthpiece portion configured for insertion into the mouth of a user for delivery of an aerosol generated by the aerosol consumable device, the mouthpiece portion having a top surface comprising two or more crescent-shaped openings arranged on opposite sides of an aerosol cap having a closed end;
   at a second end, opposite the first end, a connecting portion configured to be attached to a controller portion of an aerosol delivery device;
   a liquid absorbing insert positioned within the mouthpiece portion between the first end and the second end; and
   an aerosol tube positioned between the second end and the liquid absorbing insert;
   wherein the liquid absorbing insert comprises an absorbent material and defines an internal aerosol channel, and wherein, upon a draw on the mouthpiece portion by the user, a first portion of the aerosol generated by the aerosol consumable device travels through the internal aerosol channel of the liquid absorbing insert and through the two or more crescent-shaped openings, and
   wherein the aerosol tube is configured to direct accumulated droplets along an inner surface of the aerosol tube into the liquid absorbing insert.

2. The aerosol consumable device of claim 1, wherein when positioned within the mouthpiece portion, the liquid absorbing insert has an oblong tube shape.

3. The aerosol consumable device of claim 2, wherein the aerosol tube defines a central axis substantially aligned with a central axis defined by the internal aerosol channel of the liquid absorbing insert.

4. The aerosol consumable device of claim 3, wherein the liquid absorbing insert defines a first end and a second end, wherein the aerosol tube defines a first end proximate the second end of the liquid absorbing insert, and wherein the first end of the aerosol tube extends outwardly such that an inner diameter of the first end of the aerosol tube proximate the liquid absorbing insert is greater than a maximum diameter of the internal aerosol channel of the liquid absorbing insert.

5. The aerosol consumable device of claim 3, wherein the liquid absorbing insert defines a first end and a second end, wherein the aerosol tube defines a first end proximate the second end of the liquid absorbing insert, and wherein the first end of the aerosol tube extends outwardly such that an inner diameter of the first end of the aerosol tube is substantially the same as a maximum diameter of the internal aerosol channel of the liquid absorbing insert.

6. The aerosol consumable device of claim 1, wherein the aerosol cap further defines an open end opposite the closed end thereby creating a cavity in the aerosol cap, and wherein the cavity is configured to trap a second portion of the aerosol generated by the aerosol consumable device.

7. The aerosol consumable device of claim 6, wherein the aerosol cap defines a sidewall between the closed end and the open end.

8. The aerosol consumable device of claim 7, wherein the liquid absorbing insert defines a first end and a second end, wherein the first end of the liquid absorbing insert is located downstream from the second end of the liquid absorbing insert, and wherein the open end of the aerosol cap is located downstream from the first end of the liquid absorbing insert.

9. The aerosol consumable device of claim 7, wherein the liquid absorbing insert defines a first end and a second end, wherein the first end of the liquid absorbing insert is located downstream from the second end of the liquid absorbing insert, and wherein the first end of the liquid absorbing insert is located proximate the open end of the aerosol cap.

10. The aerosol consumable device of claim 7, wherein the liquid absorbing insert defines a first end and a second end, wherein the first end of the liquid absorbing insert is located downstream from the second end of the liquid absorbing insert, and wherein the first end of the liquid absorbing insert is located downstream from the open end of the aerosol cap.

11. The aerosol consumable device of claim 6, wherein the cavity of the aerosol cap includes a plug configured to absorb the second portion of the aerosol.

12. The aerosol consumable device of claim 6, wherein the aerosol cap defines a sidewall between the closed end and the open end, and wherein a portion of an outer surface of the sidewall is chamfered.

13. The aerosol consumable device of claim 12, wherein the chamfered portion of the outer surface of the sidewall is located at the open end of the aerosol cap and is configured to direct the first portion of the aerosol through the crescent-shaped openings.

14. The aerosol consumable device of claim 12, wherein the chamfered portion of the outer surface of the sidewall is located at the closed end of the aerosol cap and is configured to direct the first portion of the aerosol into the mouth of the user.

15. The aerosol consumable device of claim 6, wherein the aerosol cap defines a sidewall between the closed end and the open end, and wherein a portion of an inner surface of the sidewall is chamfered to direct a second portion of the aerosol into the cavity.

16. The aerosol consumable device of claim 1, wherein each of the two or more crescent-shaped openings is arranged around a peripheral outer surface of the aerosol cap.

17. The aerosol consumable device of claim 1, wherein the closed end of the aerosol cap defines an outer surface, and wherein the outer surface of the closed end of the aerosol cap is raised above at least part of the top surface of the of the first end of the aerosol consumable device.

18. The aerosol consumable device of claim 1, wherein the aerosol cap has a substantially cylindrical shape.

19. The aerosol consumable device of claim 1, wherein the first end of the aerosol consumable device has a substantially oblong shape defining an oblong dimension and an end axis substantially bisecting the oblong dimension, and wherein the two or more crescent-shaped openings are symmetrically arranged on opposite sides of the aerosol cap and substantially aligned with the end axis.

20. The aerosol consumable device of claim 1, wherein the mouthpiece portion further defines a perimeter surface located at the first end of the aerosol consumable device, and wherein the perimeter surface is raised above at least part of the top surface.

21. An aerosol consumable device comprising:
- at a first end, a mouthpiece portion configured for insertion into the mouth of a user for delivery of an aerosol generated by the aerosol consumable device, the mouthpiece portion having a top surface comprising one or more openings;
- at a second end, opposite the first end, a connecting portion configured to be attached to a controller portion of an aerosol delivery device;
- a liquid absorbing insert positioned within the mouthpiece portion between the first end and the second end; and
- an aerosol tube positioned between the second end and the liquid absorbing insert;
- wherein the liquid absorbing insert comprises an absorbent material and defines an internal aerosol channel, and wherein, upon a draw on the mouthpiece portion by the user, a first portion of the aerosol generated by the aerosol consumable device travels through the internal aerosol channel of the liquid absorbing insert and through the one or more openings, and
- wherein the aerosol tube is configured to direct accumulated droplets along an inner surface of the aerosol tube into the liquid absorbing insert.

* * * * *

UNITED STATES PATENT AND TRADEMARK OFFICE
CERTIFICATE OF CORRECTION

| | | |
|---|---|---|
| PATENT NO. | : 12,144,377 B2 | Page 1 of 1 |
| APPLICATION NO. | : 17/449690 | |
| DATED | : November 19, 2024 | |
| INVENTOR(S) | : Jason M. Short et al. | |

It is certified that error appears in the above-identified patent and that said Letters Patent is hereby corrected as shown below:

On the Title Page

In Column 2, item (56) under "Foreign Patent Documents," Line 3, delete "CN" and insert -- EP --.

In the Claims

In Column 30, in the fourth and fifth Lines of Claim 17, delete "of the of the" and insert -- of the --.

Signed and Sealed this
Twenty-seventh Day of May, 2025

Coke Morgan Stewart
*Acting Director of the United States Patent and Trademark Office*